(12) United States Patent
Vela Hernández et al.

(10) Patent No.: US 9,757,358 B2
(45) Date of Patent: Sep. 12, 2017

(54) SIGMA LIGANDS FOR POTENTIATING THE ANALGESIC EFFECT OF OPIOIDS AND OPIATES IN POST-OPERATIVE PAIN AND ATTENUATING THE DEPENDENCY THEREOF

(75) Inventors: José Miguel Vela Hernández, Barcelona (ES); Daniel Zamanillo-Castanedo, Barcelona (ES)

(73) Assignee: LABORATORIOS DEL DR. ESTEVE, S.A., Barcelona (ES)

( * ) Notice: Subject to any disclaimer, the term of this patent is extended or adjusted under 35 U.S.C. 154(b) by 420 days.

(21) Appl. No.: 13/574,121

(22) PCT Filed: Feb. 4, 2011

(86) PCT No.: PCT/EP2011/051644
§ 371 (c)(1),
(2), (4) Date: Jul. 19, 2012

(87) PCT Pub. No.: WO2011/095585
PCT Pub. Date: Aug. 11, 2011

(65) Prior Publication Data
US 2012/0289508 A1    Nov. 15, 2012

(30) Foreign Application Priority Data
Feb. 4, 2010    (EP) .................................. 10382023

(51) Int. Cl.
| A61K 31/4152 | (2006.01) |
| A61K 31/137 | (2006.01) |
| A61K 31/485 | (2006.01) |
| A61K 45/06 | (2006.01) |

(52) U.S. Cl.
CPC ........ *A61K 31/4152* (2013.01); *A61K 31/137* (2013.01); *A61K 31/485* (2013.01); *A61K 45/06* (2013.01)

(58) Field of Classification Search
CPC ............ A61K 31/4162; A61K 2300/00; A61K 31/137; A61K 31/4152; A61K 31/485; A61K 31/5377; A61K 45/06
See application file for complete search history.

(56) References Cited

U.S. PATENT DOCUMENTS

| 2,908,677 A | 10/1959 | Straley |
| 3,514,439 A | 5/1970 | Walter et al. |
| 3,980,675 A | 9/1976 | Venturella et al. |
| 4,024,175 A | 5/1977 | Satzinger et al. |
| 4,207,392 A | 6/1980 | Shiao et al. |
| 4,234,479 A | 11/1980 | Mennicke et al. |
| 4,234,616 A | 11/1980 | Shu et al. |
| 4,337,263 A | 6/1982 | Techer et al. |
| 5,948,777 A | 9/1999 | Bender et al. |
| 6,057,371 A | 5/2000 | Glennon |
| 6,100,259 A | 8/2000 | Xiang et al. |
| 6,166,072 A | 12/2000 | Bell et al. |
| 6,492,529 B1 | 12/2002 | Kapadia et al. |
| 6,509,367 B1 | 1/2003 | Martin et al. |
| 7,091,257 B2 | 8/2006 | Greer, IV |
| 7,105,646 B2 | 9/2006 | Chamberlain et al. |
| 7,696,199 B2 | 4/2010 | Laggner et al. |
| 7,799,782 B2 | 9/2010 | Munson et al. |
| 7,988,966 B2 | 8/2011 | Pavone |

(Continued)

FOREIGN PATENT DOCUMENTS

| EP | 0248594 A2 | 12/1987 |
| EP | 0414289 A1 | 2/1991 |

(Continued)

OTHER PUBLICATIONS

Arafa et. al., Journal of Medicinal Chemistry, 2005, American Chemical Society, vol. 48, pp. 5480-5488.*
Dosen-Micovic et. al., Bioorganic and Medicinal Chemistry, 2006, Elsevier, vol. 14, pp. 2887-2895.*
Chien, Chih-Cheng and Pasternak, G.W., "Selective Antagonism of Opioid Analgesia by a Sigma System", The Journal of Pharmacology and Experimental Therapeutics, 1994, vol. 271, No. 3, pp. 1583-1590.
Chien, Chih-Cheng and Pasternak, G.W., "Sigma antagonists potentiate opioid analgesia in rats", Neuroscience Letters, 1995, vol. 190, No. 2, pp. 137-139.

(Continued)

*Primary Examiner* — Sarah Pihonak
(74) *Attorney, Agent, or Firm* — Troutman Sanders LLP

(57) ABSTRACT

The invention refers to a combination comprising a sigma ligand of formula (I) and an opioid or opiate for use in the prevention and/or treatment of pain developed as a consequence of surgery, especially peripheral neuropathic pain, allodynia, causalgia, hyperalgesia, hyperesthesia, hyperpathia, neuralgia, neuritis or neuropathy. The invention also refers to the sigma ligands of formula (I) for use in potentiating the analgesic effect of an opioid or opiate and/or for decreasing the dependency induced thereby when said opioid or opiate is used in the prevention and/or treatment of pain developed as a consequence of surgery.

18 Claims, 8 Drawing Sheets

(56) References Cited

U.S. PATENT DOCUMENTS

| | | | |
|---|---|---|---|
| 8,193,223 B2 | 6/2012 | Jagerovic et al. | |
| 8,293,740 B2 | 10/2012 | Laggner et al. | |
| 8,314,096 B2 | 11/2012 | Laggner et al. | |
| 8,470,867 B2 | 6/2013 | Laggner et al. | |
| 8,492,425 B2 | 7/2013 | Jover et al. | |
| 8,877,753 B2 | 11/2014 | Buschmann | |
| 2001/0036951 A1* | 11/2001 | Farrar et al. | 514/326 |
| 2003/0144309 A1 | 7/2003 | Choon-Moon | |
| 2005/0020483 A1 | 1/2005 | Oksenberg | |
| 2006/0106068 A1 | 5/2006 | Laggner | |
| 2007/0208134 A1 | 9/2007 | Hunter et al. | |
| 2008/0058362 A1 | 3/2008 | Singh et al. | |
| 2008/0125416 A1 | 5/2008 | Laggner et al. | |
| 2008/0161604 A1 | 7/2008 | Calvani et al. | |
| 2009/0018151 A1 | 1/2009 | Fink | |
| 2009/0264442 A1 | 10/2009 | Cuberes-Altisent et al. | |
| 2009/0325975 A1 | 12/2009 | Buschmann | |
| 2010/0081659 A1 | 4/2010 | Laggner | |
| 2010/0190078 A1 | 7/2010 | Rapaport et al. | |
| 2010/0190780 A1 | 7/2010 | Laggner et al. | |
| 2010/0190781 A1 | 7/2010 | Laggner et al. | |
| 2010/0240711 A1 | 9/2010 | Takada et al. | |
| 2011/0112095 A1 | 5/2011 | Buschmann et al. | |
| 2011/0269727 A1 | 11/2011 | Toledano | |
| 2012/0141606 A1 | 6/2012 | Baeyens-Cabrera et al. | |
| 2012/0232093 A1 | 9/2012 | Cuberes-Altisent et al. | |
| 2012/0283262 A1 | 11/2012 | Soler Ranzani et al. | |
| 2012/0302568 A1 | 11/2012 | Vela-Hernandez et al. | |
| 2012/0316336 A1 | 12/2012 | Berenguer-Maimo et al. | |
| 2013/0109692 A1 | 5/2013 | Vela-Hernandez et al. | |
| 2013/0143884 A1 | 6/2013 | Cuberes-Aitisent et al. | |
| 2013/0158033 A1 | 6/2013 | Hernandez et al. | |
| 2013/0324535 A1 | 12/2013 | Zamanillo-Castanedo et al. | |
| 2015/0018354 A1 | 1/2015 | Buschmann et al. | |
| 2016/0220575 A1 | 8/2016 | Baeyens-Cabrera et al. | |

FOREIGN PATENT DOCUMENTS

| | | |
|---|---|---|
| EP | 0431943 A2 | 6/1991 |
| EP | 0445974 A2 | 9/1991 |
| EP | 0518805 A1 | 12/1992 |
| EP | 0529973 A1 | 3/1993 |
| EP | 0441333 B1 | 5/1994 |
| EP | 0975648 A1 | 2/2000 |
| EP | 1 130 018 A1 | 9/2001 |
| EP | 1130018 A1 | 9/2001 |
| EP | 1634872 A1 | 3/2006 |
| EP | 1634873 A1 | 3/2006 |
| EP | 1829866 A1 | 9/2007 |
| EP | 1829875 A1 | 9/2007 |
| EP | 1847542 A1 | 10/2007 |
| EP | 1787679 A1 | 11/2008 |
| EP | 2090311 A1 | 8/2009 |
| EP | 2112139 A1 | 10/2009 |
| EP | 2 116 539 A1 | 11/2009 |
| EP | 2113501 A1 | 11/2009 |
| EP | 2116539 | 11/2009 |
| EP | 2353598 A1 | 8/2010 |
| EP | 2254579 A1 | 12/2010 |
| EP | 2353591 A1 | 8/2011 |
| EP | 2361904 A1 | 8/2011 |
| EP | 2415471 A1 | 2/2012 |
| EP | 2292236 A1 | 3/2012 |
| EP | 2335688 A1 | 6/2012 |
| EP | 2460519 A1 | 6/2012 |
| EP | 2460804 A1 | 6/2012 |
| EP | 2524694 A1 | 11/2012 |
| EP | 2395003 A1 | 12/2012 |
| EP | 2426111 A1 | 3/2013 |
| EP | 2426112 A1 | 3/2013 |
| EP | 2792352 A1 | 10/2014 |
| EP | 2818166 A1 | 12/2014 |
| EP | 3043795 A1 | 7/2016 |
| EP | 3082790 A1 | 10/2016 |
| ES | 2251316 A1 | 10/2004 |
| FR | 2301250 A1 | 9/1976 |
| FR | 2472564 A1 | 7/1981 |
| GB | 1088973 A1 | 10/1967 |
| GB | 1496411 A1 | 12/1977 |
| GB | 2026482 A1 | 7/1987 |
| IL | 151533 B | 3/2008 |
| JP | 1992/364129 | 12/1992 |
| JP | 10036259 | 2/1998 |
| JP | 10055048 | 2/1998 |
| JP | 2004-196678 | 7/2004 |
| JP | 2008/510767 | 4/2008 |
| JP | 2008/179541 | 8/2008 |
| RU | 2218187 C2 | 10/2003 |
| RU | 2322977 C1 | 4/2008 |
| RU | 2382646 C1 | 2/2010 |
| SU | 11248 A1 | 9/1929 |
| WO | WO-91/09594 A1 | 7/1991 |
| WO | WO-92/09560 A1 | 6/1992 |
| WO | WO-93/23383 A1 | 12/1995 |
| WO | 9616063 A1 | 5/1996 |
| WO | 9846618 A1 | 10/1998 |
| WO | WO 98/46618 | 10/1998 |
| WO | WO-99/01444 A1 | 1/1999 |
| WO | WO-99/21824 A1 | 5/1999 |
| WO | WO-99/31057 A1 | 6/1999 |
| WO | WO-99/31074 A2 | 6/1999 |
| WO | WO-99/31075 A1 | 6/1999 |
| WO | 9959409 A1 | 11/1999 |
| WO | WO-99/61424 A1 | 12/1999 |
| WO | WO-00/31020 A1 | 2/2000 |
| WO | WO-00/20005 A1 | 4/2000 |
| WO | WO 00/27394 | 5/2000 |
| WO | WO-00/40275 A2 | 7/2000 |
| WO | WO-00/73259 A1 | 12/2000 |
| WO | WO-00/73296 A2 | 12/2000 |
| WO | WO-00/73300 A1 | 12/2000 |
| WO | WO-02/085839 A1 | 10/2002 |
| WO | WO-02/092573 A2 | 11/2002 |
| WO | WO-02/102387 A1 | 12/2002 |
| WO | WO-03/080183 A1 | 10/2003 |
| WO | WO-2004/016592 A1 | 2/2004 |
| WO | WO-2004/017961 A1 | 3/2004 |
| WO | WO-2004/046129 A2 | 6/2004 |
| WO | WO-2005/061462 A2 | 7/2005 |
| WO | WO-2006/010587 A1 | 2/2006 |
| WO | 2006021462 A1 | 3/2006 |
| WO | 2006027221 A1 | 3/2006 |
| WO | WO-01/634872 A1 | 3/2006 |
| WO | WO 2006/021462 A1 | 3/2006 |
| WO | WO-2006/021463 A1 | 3/2006 |
| WO | WO/2006-027221 A1 | 3/2006 |
| WO | WO-2006/118307 A1 | 11/2006 |
| WO | WO-2007/002559 A1 | 1/2007 |
| WO | WO-2007/025613 A2 | 3/2007 |
| WO | WO-2007/046550 A1 | 4/2007 |
| WO | WO-2007/079086 A1 | 7/2007 |
| WO | WO-2007/090661 A2 | 8/2007 |
| WO | 2007/098953 A1 | 9/2007 |
| WO | 2007/098963 A1 | 9/2007 |
| WO | WO-2007/098939 A1 | 9/2007 |
| WO | WO-2007/098964 A2 | 9/2007 |
| WO | WO-2007/108517 A1 | 9/2007 |
| WO | WO-2007/141018 A1 | 12/2007 |
| WO | WO-2008/015266 A1 | 2/2008 |
| WO | WO-2008/055932 A1 | 5/2008 |
| WO | WO-2008/108517 A1 | 9/2008 |
| WO | WO-2008-149062 A1 | 12/2008 |
| WO | WO-2009/038112 A1 | 3/2009 |
| WO | WO-2009/071657 A1 | 6/2009 |
| WO | WO-2009/103487 A1 | 8/2009 |
| WO | WO-2009/130314 A1 | 10/2009 |
| WO | WO-2009/130331 A1 | 10/2009 |
| WO | WO 2009130310 A1 * | 10/2009 |
| WO | WO-2011/095579 A1 | 1/2011 |
| WO | WO-2011/018487 A1 | 2/2011 |
| WO | WO-2011/064296 A1 | 6/2011 |
| WO | WO-2011064315 A1 | 6/2011 |
| WO | WO-2011/095585 A1 | 8/2011 |
| WO | WO-2011095584 A1 | 8/2011 |

(56) References Cited

FOREIGN PATENT DOCUMENTS

| WO | WO-2011/144721 A1 | 11/2011 |
|---|---|---|
| WO | WO-2011/147910 A1 | 12/2011 |
| WO | 2012/016980 A1 | 2/2012 |
| WO | WO-2012/019984 A1 | 2/2012 |
| WO | WO-2012/072781 A1 | 6/2012 |
| WO | WO-2012/072782 A1 | 6/2012 |
| WO | WO-2012/156497 A1 | 11/2012 |
| WO | WO-2012/158413 A1 | 11/2012 |
| WO | WO-2014/170319 A1 | 10/2014 |
| WO | WO-2014/207024 A1 | 12/2014 |
| WO | WO-2015/036470 A1 | 3/2015 |
| WO | WO-2015/091505 A1 | 6/2015 |
| WO | WO-2015/091508 A1 | 6/2015 |

OTHER PUBLICATIONS

Chichenkov, O.N. et al., "Effect of haloperidol on analgesic activity of different intracisternally and intrathecally injected opiate receptors", Farmakologiya i Toksikologiya, 1985, vol. 48, No. 4, pp. 58-61.
Mei, J. and Pasternak, G.W., "$\sigma_1$ Receptor Modulation of Opioid Analgesia in the Mouse", The Journal of Pharmacology and Experimental Therapeutics, 2002, vol. 300, No. 4, pp. 1070-1074.
Merskey, H. and Bogduk, N., IASP Classification of Chronic Pain, 2002, $2^{nd}$ edition, pp. 210-213.
Nomura, M. et al., "Studies on drug dependence (Rept 322): Attenuation of morphine-and psychostimulants-induced place preference by $\sigma_1$ receptor against SA4503", Japanese Journal of Pharmacology, vol. 79, No. Suppl., Jan. 1999, p. 224P.
Zahn, P.K. et al., "Mechanisms for Pain Caused by Incisions", Regional Anesthesia and Pain Medicine, 2002, vol. 27, No. 5, pp. 514-516.
International Search Report issued by the International Searching Authority (ISA/O.E.P.M.) on Apr. 5, 2011 in connection with International Application No. PCT/EP2011/051644.
Chih-Cheng Chien et al., "Sigma antagonists potentiate opioid analgesia in rats", Neuroscinece Letters, Limerick, IE, vol. 190, No. 2., 1995, pp. 137-139.
Nomura Mutsuko et al., "Studies on drug dependence (Rept 322): Attenuation of morphine-and psychostimulatns-induced place preference by sigmal receptor against SA4503", Japanese journal of Pharmacology, vol. 79, No. Suppl. 1 1999, p. 224P.
International Search Report issued by the International Searching Authority (ISA/O.E.P.M.) on Apr. 12, 2011 in connection with International Application No. PCT/EP2011/051644.
Buvanendran, A. et al. "Characterization of a New Animal Model for Evaluation of Persistent Postthoracotomy Pain", Anesth Analg, 2004, vol. 99, pp. 1453-1460.
Chen, S.R. et al. "Synergistic Effect between Intrathecal Non-NMDA Antagonist and Gabapentin on Allodynia Induced by Spinal Nerve Ligation in Rats", Anesthesiology, 2000, vol. 92, pp. 500-506.
Du, J. et al. "Kainate-induced Excitation and Sensitization of Nociceptors in Normal and Inflamed Rat Glabrous Skin", Neuroscience, 2006, vol. 137, pp. 999-1013.
Finnerup, N.B. et al. "The evidence for pharmacological treatment of neuropathic pain", Pain, 2010, vol. 150, pp. 573-581.
Kawamata, M. et al. "Experimental incision-induced pain in human skin: effects of systemic lidocaine on flare formation and hyperalgesia", Pain, 2002, vol. 100, pp. 77-89.
Kehlet, H. and Dahl, J.B. "Anaesthesia, surgery, and challenges in postoperative recovery", Lancet 2003, vol. 362, pp. 1921-1928.
Kehlet, H. et al. "PROSPECT: evidence-based, procedure-specific postoperative pain management", Best Practice Res Clin Anaesthesiol., 2007, vol. 21, pp. 149-159.
Levine, J.D. et al. "Desiperamide Enhances Opiate Postoperative Analgesia", Pain, 1986, vol. 27, pp. 45-49.
Max, M.B. et al. "Endogenous Monoamine Analgesic Systems: Amitriptyline in Painful Diabetic Neuropathy", Anesth. Prog., 1987, vol. 34, pp. 113-127.
Whittington, C.M. et al. "Understanding and utilising mammalian venom via a platypus venom transcriptome", J. Proteomics, 2009; vol. 72; pp. 155-164.
Acta Obstetrica Gynecologica Japonica, 2000, vol. 52(6), pp. 117-120.
Kehlet, H. et al. "Persistent Surgical Pain: Risk Factors and Prevention", Lancet, 2006, vol. 367; pp. 1618-1625.
Yasuda, M. et al. "Mast Cell Stabilization Promotes Antinociceptive Effects in a Mouse Model of Postoperative Pain", J. Pain Res., 2013, vol. 6, pp. 161-166.
Saha et al. "Spinal Mitogen-Activated Protein Kinase Phosphatase (MKP-3) is Necessary for the Normal Resolution of Mechanical Allodynia in a Mouse Model of Acute Postoperative Pain", J. Neurosci., 2013, vol. 43, pp. 17182-17187.
Laggner et al. "Discovery of High-Affinity Ligands of Sigma Receptor, ERG2, and Emopamil Binding Protein by Pharmacophore Modeling and Virtual Screening", J. Med. Chem., 2005, vol. 48, pp. 4754-4764.
Advokat C, Rutherford D: Selective antinociceptive effect of excitatory amino acid antagonists in intact and acute spinal rats. Pharmacology Biochemistry and Behavior 51(4):855-60, 1995.
Cheng Hong-Wei, "Postoperative patient-controlled analgesia", Jan. 21, 2010, Section Side Effects of Opioid Analgesicshttp://www.vhct.gov.tw/index.php?mo=HealthInfo&ac=health3_show&sn=390>, including English language translation.
Glass at al. Anesth. Analg. Mar. 1989, 68(3) 302-7: "Evaluation of pentamorphone in humans: a new potent opiate".
Wong et al. Anesth. Analg. May 1991, 72(5):656-60: "Pentamorphone for management of postoperative pain".
2007, XP002603149 Retrieved from the Internet: URL:http://web.archive.org/web/20080712205531/http://en.wikipedia.org/wiki/Opioidinduced-hyperalgesia. [retrieved on Oct. 1, 2010].
Angst, M.S. et al., "Opioid-induced Hyperalgesia: A Qualitative Systematic Review," Anesthesiology. vol. 104, pp. 570-587 (2006).
Anonymous "Opioid-Induced hyperalgesia," http://lweb.archive.org/web/20080712205531/http://en.wikipedia.org/wiki/Opioid-inducedhyperalgesia (retrieved Feb. 16, 2017).
Brennan, T.J. et al., "Characterization of a rat model of incisional pain", Pain, 1996, vol. 64, pp. 493-501.
Bryant et al., Opioids and addiction: Emerging pharmaceutical strategies for reducing reward and opponent processes, Clinical Neuroscience Research, 2005, 5, pp. 103-115.
Celerier et al., "Progressive Enhancement of Delayed Hyperalgesia Induced by Repeated Heroin Administration: A Sensitization Process," The Journal of Neuroscience. vol. 21, No. 11 pp. 4074-4080 (2001).
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London. Series B, Biological Sciences, vol. 236, No. 1283, pp. 101-113.
European Search Report dated Oct. 2, 2008 in connection with Application No. EP 08380122.
European Search Report dated Jun. 16, 2010 in connection with Application No. EP 10382023.
Guignard et al., "Acute Opioid Tolerance: Intraoperative RemifentanilIncreases Postoperative Pain and Morphine Requirement", Anesthesiology, vol. 93 pp. 409-417 (2000).
Hellewell, S.B. et al., "A sigma-likebinding site in rat pheochromocytoma (PC12) cells: decreased affinity for (+)-benzomorphans and lower molecular weight suggest a different sigma receptor form from that of guinea pig brain," Brain Research, vol. 527.
Hiranita et al., "Reinforcing effects of sigma-receptor agonists in rats trained to self-administer cocaine," J Pharmacol Exp. Ther. Feb. 2010; 332(2):515-524 (2010).
International Preliminary Report on Patentability dated Aug. 7, 2012 in connection with International Application No. PCT/EP2011/051644.
International Preliminary Report on Patentability dated Feb. 3, 2013 in connection with International Application. No. PCT/EP2011/063286.

(56) References Cited

OTHER PUBLICATIONS

International Preliminary Report on Patentability dated Oct. 26, 2010 in connection with International Application No. PCT/EP2009/054974.
International Search Report issued by International Searching Authority dated Jan. 31, 2012 in connection with International Application No. PCT/EP2011/063286.
Kehlet, H. et al. "Persistent Surgical Pain: Risk Factors and Prevention," Lancet, 2006, vol. 367; pp. 1618-25.
Lee, M. et al., "A Comprehensive Review of Opioid-Induced Hyperalgesia," Pain Physician. vol. 14 pp. 145-161 (2011).
Leitner et al., "Regional variation in the ratio of o1 to a2 binding in rat brain," European Journal of Pharmacology, vol. 259, pp. 65-69 (1994).
Levine, J.D. et al., "Desiperamide Enhances Opiate Postoperative Analgesia", Pain, 1986, vol. 27, pp. 45-49.
Lytle et al. "Effects of long-term corn consumption on brain serotonin and the response to electric shock," Science vol. 190, pp. 692-694 (1975).
Mao, J., "Opioid-induced abnormal pain sensitivity: implications in clinical opioid therapy," Pain. vol. 100 pp. 213-217 (2002).
Merskey, H. et al., IASP Classification of Chronic Pain, 2002, 2nd edition, pp. 210-213.
Office Action and Search Report corresponding to Taiwanese Patent Application No. 100127236 (Translation) [undated].
Prasad et al., "Exon-Intron Structure, Analysis of Promoter Region, and Chromosomal Localization of the Human Type 1 Sigma Receptor Gene," Journal of Neurochemistry. vol. 70, pp. 443-451 (1998).
Quirion et al., "A proposal for the classification of sigma binding sites," Trends pharmacal. Sci. vol. 13 pp. 85-86 (1992).
Ronsisvalle et al., "Opioid and sigma receptor studies. New development in the design of selective sigma ligands," Pure Appl. Chem. vol. 73, No. 9 pp. 1499-1509 (2001).
Sandford, M., et al.; Pain Physician 2009; 12:679-684.
Silveverman, M., "Opioid Induced Hyperalgesia: Clinical Implications for the Pain Practitioner," Pain Physician. vol. 12, pp. 679-684 (2009).
Smith M.T., "Opioid-induced hyperalgesia, opioid rotation and opioid combinations," Acute Pain. vol. 10, pp. 199-200 (2008) [Abstract].
Trescot et al., "Opioids in the Management of Chronic Non-Cancer Pain: An Update of American Society of the Interventional Pain Physicians' (ASIPP) Guidelines," Pain Physician. Opioids Special Issue: 11 pp. S5-S62 (2008).
Wang, "Opioid-induced hyperalgesia", Chinese Journal of Pain Medicine, 14(3), pp. 129-130 (2008).
Written Opinion of the International Searching Authority issued on Feb. 5, 2013 in connection with International Application No. PCT/EP2011/063286.
Written Opinion of the International Searching Authority dated Jun. 17, 2009 in connection with International Application No. PCT/EP2009/054974.
Yasuda, M. et al., "Mast Cell Stabilization Promotes Antinociceptive Effects in a Mouse Model of Postoperative Pain," J. Pain Res., 2013, vol. 6, pp. 161-166.
Zahn, P.K. et al., "Mechanisms for Pain Caused by Incisions", Regional Anesthesia and Pain Medicine, 2002, vol. 271 No. 5, pp. 514-516.
Cao, J., et al., "Dual Probes for the Dopamine Transporter and sigmal Receptors: Novel Piperazinyl Alkyl-bis(4-fluorophenyl)amine Analogues as Potential Cocaine-Abuse Therapeutic Agents", J. Med. Chem, No. 13, Mar. 20, 1946, pp. 2589-2598.
Nomura, M., et al., "Studies on drug dependence (Rep!. 322): Attenuation of morphine- and psychostimulants-induced place preference by sigma1 receptor agonist SA4503", Japanese Journal of Pharmacology, The Japanese Pharmacological Society, Kyoto, JO, vol. 79, No. suppl. 1, Jan. 1, 1999, p. 224P.

Izenwasser, S., et al., "Characterization of kappa-opioid receptor binding in human insular cortex", Life Sciences, Pergamon Press, Oxford, GB, vol. 65, No. 9, Jul. 23, 1999, pp. 857-862.
Osipova, N.A., "Tramadol (Tramal) in the Treatment of Acute and Chronic Pain Syndromes," Russky Meditsinsky Zhurnal (Russian Medicinal Journal), Feb. 25, 2003, No. 4, Sections: Pulmonology: Selected Lectures for Family Physicians (Retrieved from the Internet: URL <rmj.ru/number_36.htm).
Grahame-Smith, D.G., et al., Oxford textbook on clinical pharmacology and drug therapy M., "Meditsina", 2000, pp. 658-661, Chapter "Narcotic analgesics".
Drug encyclopedia M., RLS 2001, pp. 572-573, articles "Morphine", "Morphine Sulfate".
Consilium MedSigma-receptors: new potentials of the treatment of depressions. Consilium Medicumicum 2012, vol. 14, No. 2 (found in the Internet: URL<new.Consiliummedicum.com/magazines/cm/medicum/article/21505, paragraphs 4-8).
Pirim, A., et al., "Addition of ketamine infusion to patient controlled analgesia with intravenous morphine after abdominal hysterectomy" Agri Jan. 2006; 18(1):52-8 Abstract.
Chien et al., "Selective Antagonism of Opioid Analgesia by a Sigma System", J. Pharmacol. Exp. Ther.; 1994; 271; pp. 1583-1590.
Mei et al., "Receptor Modulation of Opioid Analgesia in the Mouse", J. Pharmacol Exp. Ther.; 2002; 300(4); pp. 1070-1074.
Carlsson et al., "Interaction of pentobarbital and morphine in the tail-flick test performed on rates: synergism at the spinal and antagonism at the supraspinal level", NeuroSci. Lett.; 1986; 71; pp. 356-360.
Janicki et al., "Detection of Antagonist Activity for Narcotic Analgesics in Mouse Hot-Plate Test" Pharmacol. Biochem. Behavior, 1979; 10(4); pp. 623-626.
Chien, C., et al., "Sigma antagonists potentiate opioid analgesia in rats," Neuroscience Letters, vol. 190, No. 2, 1995, pp. 137-139.
International Search Report for PCT/EP2009/054974, dated Jun. 17, 2009.
"Chemotheraphy at home, pain and its treatment", Soins, Office De Publicite Generale, Paris, FR, (Sep. 1, 1989), No. 528, ISSN 0038-0814, pp. 17-20, XP009107313 [A] 1-16.
Aapro, M. et al., "Anticipatory Nausea and Vomiting", Support Care Cancer, 2005, vol. 13, pp. 117-121.
Abadias, M. et al. "Saftey, Tolerability and Pharmacokinetics of Single and Multiple Doses of a Novel Sigma-1 Receptor Antagonist in Three Randomized Phase l studies," British Journal of Clinical Pharmacology, 2012, 75:1, 103-117.
Abbott, C, A., et ale "The North-West Diabetes Foot. Care Study: incidence of, and risk .factors for, new diabetic foot ulceration in a community-based patient cohort", Diabetic Medicine, vol, 19, 2002, pp. 377-384.
Abraham, D.J., et al., "Burger's Medicinal Chem istry: Drug Discovery and Development" 7th edition, 8 volume set, 2010.
Abrams, P., et al., "The standardisation of terminology of lower urinary tract function: report from the standardisation sub-committee of the International Continence Society", Neurology and Urodynamics, 21, 2002, pp. 167-178.
Alberts, D.S., et al., "Cisplatin-associated neurotoxicity: can it be prevented?" Anti-cancer Drugs, 1995, vol. 6, pp. 369-383.
Almerico, AM., "1-Methyl-3H-pyrazolo[1, 2-a]benzo[1, 2, 3, 4] tetrazin-3-ones: Design, synthesis and biological activity of new antitumor agents", Journal of Medicinal Chemistry, vol. 48, 2005, pp. 2859-2866.
Anderson, B. D. et al,, "Preparation of Water-Soluble Compounds Through Salt Formation" The Practice of Medicinal Chemistry, Chapter 34, pp. 739-754 (1996).
Anton, E., "Delayed toxicity of cyclophosphamide on the bladder of DBA/2 and C57BL/6 female mouse," Int. J. Exp. Path., 83, 2002, pp. 47-53.
Arthritis [online], [retrieved on Nov. 20, 2007]. Retrieved from the Internet, URL; http://www.nlm.nih.gov/medlineplus/ency/article/001243.htm>.
Argyrioul, A.A., et al., "Bortezomib-induced peripheral neuropathy in multiple myelorna: a comprehensive review of the literature", Blood, 2008, vol. 112, No. 5, pp. 1593-1599.

(56) References Cited

OTHER PUBLICATIONS

Asano, T., et al. Antinociception by epidural and systemic alpha(2)adrenoceptor agonists and their binding affinity in rat spinal cord and brain, *Anesth Anal g.* 2000; 90 (2): 400-407.
Baraldi, et al., "Ethyl 2, 4-Dioxoalkanoates as Starting Materials for a Convenient Route to 3(2H)Furanones and 3(2H) Furanimines", Tetrahedron, vol. 43, No. 1, pp. 235-242, 1987.
Baraldi, et al., "Ethyl 5-Substituted-3-Isoxazolecarboxylates as Starting Materials for a Convenient Route to 3(2H) Furanones and 3(2H)Iminofuranes", Tetrahedron Lett., 25(38), pp. 4313-4316; 1984.
Barnes, J.M. et al., "Reserpine, Para-Chlorophenylalanine and Fenfluramine Antagonise Cisplatin-Induced Emesis in the Ferret", Neuropharmacology, 1988, vol. 27, No. 8, pp. 783-790.
Batson, et al., "a-Hydroxy Cyclopentenones from a-Diketones", Organic Letters, vol. 7, No. 13, pp. 2771-2774, 2005.
Beaudegnies, R., et al. "Design and synthesis of novel spirocyclopropyl cyclohexane-1,3-diones and -1,3,5-triones for their incorporation into potent HPPD inhibitors", Tetrahedron Letters, 2010, vol. 51, pp. 2741-2744.
Bennett, G, J. "Pathophysiology and Animal Models of Cancer-Related Painful Peripheral Neuropathy", The Oncologist, 2010, 15 (suppl2), pp. 9-12.
Berge, S.M. et al., "Pharmaceutical Salts," Journal of Pharmaceutical Sciences, 1977. vol. 66, No. 1, pp. 1-19.
Ban, K., et al., "Characterization of cyclophosphamide cystitis, a model of visceral and referred pain, in the mouse: species and strain differences,", J Urol., (2003), vol. 170, No. 3, pp. 1008-1012.
Batting, R,M.; Clinical Infectious Diseases, 2000, 31, S202-10.
Boulton, A.J.M., et al., "Diabetic Neuropathies" Diabetes Care, vol. 28, No. 4, Apr. 2005, pp. 956-962.
Bowen W. D., Pharmaceutica *Acta Helvetiae*; 2000; 74:211-218.
Brammer et al. in European Journal of Pharmacology, 553, 141-145 (2006).
Brussee, et al., Diabetes, 2008, 57:1664-1673, "Distal Degenerative Sensory Neuropathy in a Long-Term Type 2 Diabetes Rat Model".
Bryans, J.S., et al., "3-substituted GABA analogs with central nervous system activity: a review," Med Res Rev, 19, 1999, pp. 149-177.
Bryans, J.S., et al., "Identification of novel ligands for the oabapentin binding site on the alpha-2-delta subunit of a calcium channel and their evaluation as anticonvulsant agents", J. Med. Chem. 41, 1998, pp. 1838-1845.
Buerkle, H., Yaksh, T. L. Pharmacological evidence for different alpha 2-adrenergic receptor sites mediating analgesia and sedation in the rat, *Br J Anaesth*, 1998; 81 (2): 208-215.
Bura, S.A. et al., "Evaluation of the Effect of the Selective Sigma-1 Receptor Antagonist SIRA in Neuropathic Pain Using an Operant Model", Eur J. Pain Supplements 2010, vol. 4, p. 49 (Abstract Only).
Cancer [online], [retrieved on Jul. 6, 2007]. Retrieved from the Internet, URL; http://www.nim.nih.gov/medlineplus/cancer.html/>.
Lala et al., "Role of Nitric Oxide in Tumor Progression: Lessons from Experimental Tumors." Cancer and Metastasis Reviews, 17(1), 91-106, 1998.
Carrle, et: al., Int Orthopaedics vol. 30, pp. 445-451. publication year: 2006.
Carter, N., et al., "Duloxetine: a review of its use in the treatment of generalized anxiety disorder.", CNS Drugs 2009, (2009), vol. 23, No. 6, ISSN 1172-7047, pp. 523-541, ISSN: 1172-7047.
Case 07 "Joint Pain and Muscle Pain", Nurse Beans—Smart Nurse, Nov. 2007, vol. 9, No. II, pp. 1238-1239.
Cepeda, MS, "Comparison of Morphine, ketorolac, and their combination for postoperative pain: results form a large, randomized, double-blind trial", anesthesiology, 2005, vol. 103, No. 6, pp. 1225-1232.
Cersosimo, R.J., "Oxaliplatin-Associated Neuropathy: A Review", The Annals of Pharmacotherapy, 2005 vol. 39 pp. 128-135.
Chaplan S. R., et al., "Quantitative assessment of tactile allodynia in the rat paw", J. Neurosci. Methods, (1994), vol. 53, pp. 55-63.

Chaudhry, V., et al., "Bortezornib and thalidomide-induced subacute demyelinating polyneuropathy," Clinical Neurophysiology, 2009, vol. 120, p. e111.
Chaudhry, V., et al., "Peripheral Neuropathy from Taxol and Cisplatin Combination Chemotherapy: Clinical and Electrophysiological Studies", Annals of Neurology, 1994, vol. 35, No. 3, pp. 304-311.
Cheng, et al., Modern Bone Science, Modern Orthopaedics, "14.2.2 Drug Analgesia," p. 164, 2010, including English translation.
Chen, D., et al., "Development and application of rodent models for type 2 Diabetes", Diabetes, Obesity and Metabolism, vol. 7, 2005, pp. 307-317.
Cherry, N., "Opioids and the Management of Cancer Pain", Eur. J. Cancer Supplement 2005, vol. 3, pp. 61-75.
Non-Final Office Action issued on Feb. 2, 2009 in related U.S. Appl. No. 11/574,361 citing STN-search report report JP10055048 (p. 8).
Clark, J.B., et al., "The Diabetic Zucker Fatty Rat (41611)", Proceedings of the society for experimental Biology and Medicine, 1983, vol. 173, pp. 68-75.
Cobos, E. J., et al., Pharmacology and therapeutic potential of Sigma(1) receptor ligands. Curr. Neuropharmacol. 2008; 6, 344-366.
Final Office Action dated Nov. 29, 2007 in related priority U.S. Appl. No. 10/978,250.
Final Office Action dated Oct. 20, 2008 in related priority U.S. Appl. No. 10/978,250.
Non-Final Office Action dated Apr. 16, 2008 in related priority U.S. Appl. No. 10/978,250.
Non-Final Office Action dated Jun. 14, 2007 in related priority U.S. Appl. No. 10/978,250.
Requirement for Restriction/Election dated Apr. 5, 2007 in related priority U.S. Appl. No. 10/978,250.
Coxon, et al., "Acid-catalysed Rearrangements of trans- and cis-1-Acetoxy-3,4-epoxypentane and 1-Acetoxy-4,5- epoxyhexane", J. Chem. Soc. Chem. Cornmun., 8, pp. 261-262, 1973.
Crawford, K.W. et al., "Sigma-2 Receptor Agonists Activate a Novel Apoptotic Pathway and Potentiate Antineoplastic Drugs in Breast Tumor cell Lines1," Cancer Research, 2002, vol. 62, 313-322.
D'Amour, F. E. And Smith, D. L. A method for determining the loss of pain sensation, *J. Pharmacal. Exp. Ther.* 1941; 72:74-79.
Dani, et al. (2007) The local antinociceptive effects of paracetamol in neuropathic pain are mediated by cannabinoid receptors. European Journal of Pharmacology 573(1-3):214-215.
Danziger, et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London. Series B, Biological Sciences, vol. 236, No. 1283, pp. 101-113.
Daousi, C., et al., "Chronic painful peripheral neuropathy in an urban community: a controlled comparison of people with and without diabetes", Diabetic Medicine, vol. 21, 2004, pp. 976-982.
Dapeng Li "The Role of Glial Cells in . . . Pain", Thesis of Huazhong, University of Science and Technology, 2006, p. 24; Publication Date: Feb. 19, 2008.
Database WPI Week 200451 Thomson Scientific, London, GB; AN 2004-529624-& JP 2004 196678 A (Dainippon Pharm Co Ltd) Jul. 15, 2004. (Ju. 15, 2004).
Dauben, W., et al., "Organic Reactions at High Pressure Preparation of Wittig Phosphonium Salts at Ambient Temperature", J, Org. Chem., 1984, vol. 49, pp. 4293-4295.
Davies, A., et al., "Functional biology of the alpha-2-delta subunits of voltage-gated calcium channels,"trends in Pharmacological Sciences, vol. 28, No. 5, 2007, pp. 220-228.
DeHaven-Hudkins, et al, "Characterization of the binding of [H](+)-pentazocine to o' recognition sites in guinea pig brain," European Journal of Pharmacology- Molecular Pharmacology Section, 1992, vol. 227, pp. 371-378.
Dewar, "Diethyl-[3-(5-methyl-1-phenyl-1H-pyrazol-3-yl)-propyl]amine", Database Beilstein, Beilstein Institute for Organic Chemistry, Frankfurt-Main, DE, Database accession No. 213356, XP002605612 [X] 1-3,5,6,9.

(56) References Cited

OTHER PUBLICATIONS

Dewar, M. J. S., "Attempts to find new Antimalarials. Part XXI" Journal of the Chemical Society, (1944), pp. 615-619.

Dias, V. C., et al., Clinical experience with transdermal clonidine in African-American and Hispanic-American patients with hypertension: evaluation from a 12-week prospective, open-label clinical trial in community-based clinics, Am J Ther. 1999; 6 (1): 19-24.

Diaz, J.L. et al., "Selective Sigma-1 Receptor Antagonists: Emerging Target for the Treatment of Neuropathic Pain", Cent. Nerv. Syst. Agents in Med. Chem. 2009, vol. 9 pp. 172-183.

Díaz, J.L., et al., "Synthesis and Biological Evaluation of the 1-Arylpyrazole Class of sigma 1 Receptor Antagonists: Identification of 4-{2-[5-Methyl-1-(naphthalen-2-yl)-1H-pyrazol-3-yloxy]ethyl}morpholine (S1RA, E-52862)", Journal of Medicinal Chemistry, (Oct. 11, 2012), vol. 55, No. 19, doi:10.1021/jm3007323, ISSN 0022-2623, pp. 8211-8224, XP055094581 [Y] 1-14, 16.

Dixon, W. J., "Efficient analysis of experimental observations", Ann. Rev. Pharmacal. Toxicol., 20, 1980, pp. 441-462.

Dmitrieva, N., et al., "The role of nerve growth factor in a model of visceral inflammation", Neuroscience, vol. 78, No. 2, 1997, pp. 449-459.

Dougherty, P.M., et al, "Taxol-induced sensory disturbance is characterized by preferential impairment of myelinated fiber function in cancer patients", Pain, 2004, vol. 109, pp. 132-142.

Dugowson, et al.; Phys. Med. Rehabil. Clan. N. Am. 2006, 17, 347-354.

Dukic-Ott, A. "Production of pellets via extrusion spheronisation without the incorporation of microcrystalline cellulose; A critical review," European Journal of Pharmaceutics and Biopharmaceutics, 2009, vol. 71, pp. 38-46.

Dunlap, B., et al., "Chemotherapy-Induced Peripheral Neuropathy Measurement", The Journal of Supportive Oncology, 2006, vol. 4, 8, pp.

Dworkin R.H., "An Overview of Neuropathic Pain: Syndromes, Symptoms, Signs, and Several Mechanisms," The Clinical Journal of Pain 2002, vol, 18, pp. 343-349.

Dworkin, R.H, et A., "Recommendations for The Pharmacological Management of Neuropathic Pain: Literature Update", Mayo Cain. Proc., 2010, 85(3)(Suppl), S3-S14.

Ellenberger, F., et al., Chem. Ber., 102(10), 3260-3267, 1969.

Eghbaldar, et al., "Substances aromatisantes separation chirale par chromatographie gazeuse" Parfums, Cosmetiques, Aromes, 104, pp. 71-78, 1992.

Eisenach, J. C., et al., Intrathecal, but not intravenous, clonidine reduces experimental thermal or capsaicin-induced pain and hyperalgesia in normal volunteers; *Anesth Analg*; 1998; 87: 591-596.

Entrena, J.M., et al., "Sigma-I receptors are essential for capsaicin-induced mechanical hypersensitivity: Studies with selective sigma-1 ligands and sigma-1 knockout mice", Pain, (2009), vol. 143, pp. 252-61.

Epilepsy [online], [retrieved on Nov. 20, 2007]. Retrieved from the Internet, URL; http://www.nim.nih.gov/medlineplus/ency/article/000694.htm>.

Epstein, et al., "Oral Doxepin Rinse: The Analgesic Effect and Duration of Pain Reduction in Patients with Oral Mucositis Due to Cancer Therapy" (2006) Pain Medicine, vol. 103, No. 2, pp. 465-470.

Epstein, et al., "Oral topical doxepin rinse: analgesic effect in patients with oral mucosal pain due to cancer or cancer therapy" (2001) Oral Oncology, 37:632-637.

European Search Report dated Feb. 1, 2010 in connection with priority European Application No. EP 04077421.8.

European Search Report dated Apr. 19, 2010 in connection with European Application No. EP10382024.7.

European Search Report dated Dec. 20, 2013 in connection with European Application No. EP13382246.0.

European Search Report dated Feb. 5, 2010 in connection with European Application No. EP09382144.

European Search Report dated Jan. 31, 2011 in connection with European Patent Application No. 10382326.6.

European Search Report dated Jul. 1, 2010 in connection with European Patent Application No. EP10382025.

European Search Report dated Mar. 11, 2011 in connection with European Application No. EP10382330.8.

European Search Report dated Apr. 14, 2010 in connection with European Application No. EP09382261.

European Search Report dated May 3, 2013 in connection with European Patent Application No. EP13382140.

European Search Report dated Oct. 1, 2010 in connection with European Application No. EP10382215.1.

European Search Report dated Oct. 18, 2011 in connection with European Application No. EP11382157.3.

European Search Report dated Oct. 29, 2010 in connection with European Application No. EP10382136.

European Search Report dated Sep. 12, 2008 in connection with European Application No. EP08384006.

European Search report dated Oct. 22, 2010 by European Patent Office in connection with European Application No. EP08384006.

Falk et a., "Pain and Nociception: Mechanisms of Cancer-Induced Bone Pain", Journal Clinical Oncology, 2014, vol. 32, pp. 1647-1654.

Field, M.J., et al,, "Identification of the alpha-2-delta-1 subunit of voltage-dependent calcium channels as a molecular target for pain mediating the analgesic actions of pregabalin", PNAS, vol. 103, No. 46, Nov. 14, 2006, pp-17537-17542.

Forsyth, P.A., et al., "Prospective study of paclitaxel-induced peripheral neuropathy with quantitative sensory testing", Journal of Neuro-Oncology, 1997, vol. 35, pp. 47-53.

Friedman, J.E., et al., Altered expression of muscle glucose transporter GLUT -4 in diabetic fatty Zucker rats (ZDF/Drtfa), American Physiological Society, 1991, E782-E788.

Gabriel, A.F., Preoperative housing in an enriched environment significantly reduces the duration of post-operative pain in a rat model of knee inflammation, Neurosci. Lett. 2010, vol. 469, No. 2, pp. 219-232.

Gauchan, P., et al., "Mechanical Allodynia Induced by Pacli taxel, oxaliplatin and Vincristine: Different Effectiveness of Gabapentin and Different Expression of Voltage-Dependent Calcium Channel a26-1 subunit", Biol. Phann. Bull., 2009, vol. 32, No. 4 $f$ pp. 732-734.

Gentili, M., et al., Intra-articular morphine and clonidine produce comparable analgesia but the combination is not more effective, *Br J Anaesth.* 1997; 79 (5): 660-661.

Goblirsch, M.J., et al., "Biology of Bone Cancer Pain," Clin. Cancer Res. 2006' vol. 12 (20 Suppl.), pp. 6231s-6235s.

Goodman, et al., "The Pharmacological Basis of Therapeutics", 8th Ed.; 13-18, 1992.

Gordois, A., et al., "The Health Care Costs of Diabetic Peripheral Neuropathy in the U.S " Diabetes Care, vol. 26. No. 6. Jun. 2003, pp. 1790-1795.

Gordon, A.N., et al., "Phase 1 Dose Escalation of Paclitaxel in Patients with Advanced Ovarian Cancer Receiving Cisplatin: Rapid Development of Neurotoxicity is Dose-Limiting", Journal of Clinical Oncology, 1997, vol. 15, No. 5, pp. 1965-1973.

Gralla et al. in Annals of Internal Medicine 95(4), 414-420 (1981).

Grover, S., et al., "Role of inflammation in bladder function and interstitial cystitis", Therapeutic Advances in Urology, 3(1), 2011, pp. 19-33.

Grunberg, S, M., et al., "Incidence of Chemotherapy-induced Nausea and Emesis after Modern Antiemetics," Cancer, 2004, vol. 100, pp. 2261-2268.

Guitart, X., et al., "Sigma receptors biology and therapeutic potential", Psychopharmacology, 2004, vol. 17 4, pp. 301-319.

Haleblian, "Characterization of Habits and Crystalline Modification of Solids and Their Pharmaceutical Applications," Journal of Pharmaceutical Sciences, vol. 64. No. 8 pp. 1269-1288 (1975).

Hall, J. E., Uhrich, T. D., Ebert, T. J. Sedative, analgesic and cognitive effects of clonidine infusions in humans, *Br J Anaesth.* 2001; 86 (1): 5-11.

(56) References Cited

OTHER PUBLICATIONS

Hammack, et al., "Phase III evaluation of nortriptyline for alleviation of symptoms of cis-platinum-induced peripheral neuropathy" (2002) Pain, 98:195-203.
Hancock, et al., "Characteristics and Significance of the Amorphous State in Pharmaceutical Systems," Journal of Phamnaceutical Sciences, vol. 86, No. 1 pp. 1-12 (1997).
Hanna, Philip, "International Consultation on IC—Rome, Sep. 2004/Forging an interenational consensus: progress in painful bladder syndrome/interstitial cystitis", Int Urogynocol J, 16, 2005, pp. S2-S34.
Harden, N., et al., "Unmet Needs in the Management of Neuropathic Pain", Journal of Pain and Symptom Management, 2003, 25, 5S, S12-S17.
Hartwig, J., "Synthesis, Structure, and Reactivity of a Palladium Hydrazonato Complex: A New Type of Reductive Elimination Reaction to FormC-N Bonds and Catalytic Arylation of Benzophenone Hydrazone", Angew. Chern. Int. Ed., 1998, vol. 37. No. 15, pp. 2090-2093.
Hayashi, T., et al., "Sigma-1 receptor ligands: potential in the treatment of neuropsychiatric disorders," CNS Drugs. 2004; 18(5): 269-84.
Hecht, J. R. et al., "Prolonged Nausea and Vomiting after High Dose Chemotherapy and Autologous Peripheral Stem Cell Transplantation in the Treatment of High Risk Breast Carcinorrta," Cancer, 19971 vol. 79' pp. 1698-1702.
Herndon, et al.; Pharmacotherapy, 2008, 28(6), 788-805.
Herrstedt, J., et al., Acute emesis moderately emetogenic chemoc. herapy, Support Care Cancer, 2005, vol. 13, pp. 97-103.
Hesketh, M.' et al., "Proposal for classifying the Acute Emetogenicity of Cancer Chemotherapy", Journal of Clinical Oncology, 1997, vol. 15, pp. 103-109.
Hidaka, T., et al., W5-7 "A Basic Study of the Effect Peony Licorice Water on Paclitaxel-Induced Pain in Mice", Japan Academic Journal of Cancer Treatment, Sep. 2009, vol. 44, No. 2, p. 323 [inc. machine English language translation).
Hileman, G.A., et al., "Response surface optimization of high dose pellets by extrusion and spheronization," International Journal of Pharmaceutics, 1993, vol. 100, pp. 71-79.
Hinz et al., FASEB Journal, 2007, 7, 2343-2351.
Narujo, Hiroyuki, et al., Cancer Pain Treatment—Clinical Oral Morphine Extended-Release Tablets (once/day), 5$^{th}$, Pharma Medical, 2007, including English language translation.
Homer, et al., "Azo-aryle and Phenazine aus primaren Arylaminanionen lurch Autoxydation", Chem. Ber, 96, pp. 786-793, 1963.
Hsu, et al Toxic. Appl. Pharmac., vol. 73, No. 3, pp. 411-415, 1984.
Hudzik T. J., "Sigma Ligand-Induced Emesis in the Pigeon," Pharmacology Biochemistry & Behavior, 1991, 41(1), pp. 215-217.
Hudzik, T., et al., "o Receptor-mediated emetic response in pigeons: agonists, antagonists and modifiers", European Journal of Pharmacology, 1993, vol. 236, pp. 279-287.
!Asp Classification of Chronic Pain, 2002, 2nd edition, pp. 201-213.
International Preliminary Report of Patentability with Written Opinion of the International Searching Authority dated Nov. 27, 2012 in connection with International Application No. PCT/EP2011/058633.
International Preliminary Report of Patentability with Written Opinion of the International Searching Authority dated Feb. 14, 2012 in connection with International Application No. PCT/EP2010/061720.
International Preliminary Report of Patentability with Written Opinion of the International Searching Authority dated May 30, 2012 in connection with International Application No. PCT/EP2011/068213.
International Preliminary Report of Patentability with Written Opinion of the International Searching Authority dated Feb. 12, 2013 in connection with International Patent Application No. PCT/EP2011/063583.
International Preliminary Report of Patentability with Written Opinion of the International Searching Authority dated Aug. 7, 2012 in connection with International Application No. PCT/EP11/51643.
International Preliminary Report of Patentability with Written Opinion of the International Searching Authority dated Aug. 24, 2010 in connection with International Application No. PCT/EP2009/001109.
International Preliminary Report of Patentability with Written Opinion of the International Searching Authority dated Dec. 29, 2015 in connection with International Application No. PCT/EP2014/063360.
International Preliminary Report of Patentability with Written Opinion of the International Searching Authority dated Feb. 28, 2007 in connection with international Application No. PCT/EP2005/009375.
International Preliminary Report of Patentability with Written Opinion of the International Searching Authority dated Jun. 21, 2016 in connection with International Application No. PCT/EP2014/077996.
International Preliminary Report of Patentability with Written Opinion of the International Searching Authority dated Jun. 21, 2016 in connection with International Application No. PCT/EP2014/077992.
International Preliminary Report of Patentability with Written Opinion of the International Searching Authority dated Jun. 4, 2013 in connection with International Application No. PCT/EP2011/071584.
International Preliminary Report of Patentability with Written Opinion of the International Searching Authority dated Jun. 26, 2012 in connection with International Application No. PCT/EP2012/059232.
International Preliminary Report of Patentability with Written Opinion of the International Searching Authority dated Mar. 15, 2016 in connection with International Application No. PCT/EP2014/069370.
International Preliminary Report of Patentability with Written Opinion of the International Searching Authority dated Mar. 30, 2012 in connection with International Application No. PCT/EP2010/068256.
International Preliminary Report of Patentability with Written Opinion of the International Searching Authority dated Nov. 27, 2012 in connection with International Application No. PCT/EP2011/058224.
International Preliminary Report of Patentability with Written Opinion of the International Searching Authority dated Oct. 20, 2015 in connection with International Application No. PCT/EP2014/057608.
International Search Report dated Jul. 24, 2009 in connection with International Application No. PCT/EP2009/054981.
International Search Report dated Nov. 25, 2010 in connection with International Application No. PCT/EP2010/061720.
International Search Report dated May 4, 2011 in connection with International Application No. PCT/EP2011/051630.
International Search Report dated Aug. 31, 2011 in connection with International Application No. PCT/EP2011/063583.
International Search Report dated May 4, 2011 in connection with International Application No. PCT/EP2010/068256.
International Search Report dated Sep. 21, 2011 in connection with International Application No. PCT/EP2011/058633.
International Search Report dated Feb. 25, 2015 in connection with International Application No. PCT/EP2014/077996.
International Search Report dated Jan. 12, 2005 in connection with International Application No. PCT/EP2005/009375.
International Search Report dated Jan. 16, 2012 in connection with International Application No. PCT/EP2001/071583.
International Search report dated Jul. 7, 2009 in connection with International Application No. PCT/EP2009/001109.
International Search Report dated Jun. 26, 2012 in connection with International Application No. PCT/EP12/59232.
International Search Report dated Mar. 13, 2012 in connection with International Application No. PCT/EP2011/071584.
International Search Report dated Mar. 23, 2011 in connection with International Application No. PCT/EP2010/068213.

(56) References Cited

OTHER PUBLICATIONS

International Search Report dated Mar. 6, 2014 in connection with International Application No. PCT/EP2014/057608.
International Search report dated May 23, 2011 in connection with International Application No. PCT/EP11/51643.
International Search report dated Oct. 31, 2014 in connection with International Application No. PCT/EP2014/069370.
International Search report dated Sep. 17, 2014 in connection with International Application No. PCT/EP2014/063360.
International Search Report dated Sep. 3, 2015 in connection with International Application No. PCT/EP2014/077992.
International Search Report dated Mar. 8, 2011 in connection with International Applications No. PCT/EP2011/058224.
International Preliminary Report of Patentability with Written Opinion of the International Searching Authority dated Oct. 26, 2010 in connection with International Application No. PCT/EP2009/054981.
Isakov "The problem of pain in oncology", Russian Medicinal Journal, 2000, vol. 17, pp. 723-727.
Isomers [on-line], [retrieved on Mar. 11, 2007]. Retrieved from the Internet, URL; http://chemed.chem.purdue.edu/genchem/topicreview/bp/1organic/isomers.html>.
Jordan, K., et al. "Chemotherapy-induced nausea and vomiting: current and new standards in the antiemetic prophylaxis and treatment," Eur J Cancer. Jan. 2005; 41(2):199-205.
Jover, I., et al., "Evaluation, by a Statistically Designed Experiment, of an Experimental Grade of Microcrystalline Cellulose, Avicel 955, as a Technology to Aid to Production of Pellets with High Drug Loading," Journal of Pharmaceutical Sciences, 1996, vol. 85, No. 71 pp. 700-705.
Kaiser, et al., *Neurotransmissions*; 1991; 7(1); 1-5.
Kautio, et al., "Amitriptyline in the Prevention of Chemotherapy-induced Neuropathic Symptoms" (2009) Anticancer Research, 29:2601-2606.
Kautio, et al., "Amitriptyline in the Treatment of Chemotherapy-Induced Neuropathic Symptoms" (2008) Journal of Pain and Symptom Management, 35(1):31-39.
Kadirogiu, A.K., et al., "The effect of venlafaxine HCI on painful peripheral diabetic neuropathy in patients with type 2 diabetes mellitus.", Journal of Diabetes and Its Complications Jul.-Aug. 2008, (Jul. 2008), vol. 22, No. 4, ISSN 1873-460X, pp. 241-245, XP002721925 [Y] 1-17.
Kenakin, A., Pharmacology Primer, The Evolving Pharmacology of GPCR's, 2006, pp. 27-60.
Kerba, et al. Oct. 2010, Journal of Clinical Oncology, vol. 28, No. 33, pp. 4892-4897.
Kest, et. al., Pharmacology Biochemistry, and Behavior, 1995, Pergamon, vol. 52, No. 1, pp. 175-178.
Khouzam, H. R., et al., "Remission of Cancer Chemotherapy-induces Emesis During Antidepressant Therapy with Nefazodone", Psychosomatic Medicine, 1998, vol. 60, pp. 89-91.
Kim, et al., "Activation of the spinal sigma-1 receptor enhances NMDA- induced pain via PKC- and PKA-dependent phosphorylation of the NRI subunit in mice", Br. J. Pharmacal., 2008, vol. 154, pp. 1125-1134.
Kim, et al., Int Neurourol J.; Mar. 2016; 20(1); 13-17.
Kirchmair, R., et al., "Therapeutic Angiogenesis Inhibits or Rescues Chemotherapy-induced Peripheral Neuropathy: Taxol- and Thalidomide-induced Injury of Vasa Nervorum is Ameliorated by VEGF," Molecular Therapy, 2007, vol. 151 No. 1, pp. 69-75.
Koralewski, p., et al., Effectiveness of cyproheptadine in the management of delayed vomiting after cisplatin-based chemotherapy and the assessment of the influence of cyproheptadine on quality of lifen, Chemotherapy Dept. Rydygier Memorial Hospital, Cracow, Poland, vol. 5, pp. 499-503.
Kranz, H., et al., "Drug Release from MCC- and carrageenan-based pellets: Experiment and theory," European Journal of Pharmaceutics and Biopharmaceutics, 2009, vol. 73, pp. 302-309.
Kuloor, et. al., Age and Aging, 2006, Oxford University Press, vol. 35, pp. 639-640.
Kunz, N. R., et al., "Diabetic neuropathic pain management with venlafaxine extended release", European Neuropsychopharmacology, Elsevier Science Publishers BV, Amsterdam, NL, vol. 10, ISSN 0924-977X, (Sep. 1, 2000), p. 389, (Sep. 1, 2000), XP027389705 [Y] 1-17.
Kuruvilla et al., Arch Otolaryngol Head Neck Surg. Jan. 2009; 135(1); 101-105.
Laboratoire Roger Bellon's CAS: 87: 5959, 1977.
LaBuda, et al., (2005) Pharmacological evaluation of the selective spinal nerve ligation model of neuroFathic pain in the rat. J. Neurosci. Methods 144 (2): 175-181.
LaBudde, et al., "The Synthesis of the Mono- and Dihydroxy Derivatives of 1,2,5,6- Dibenzanthracene Excreted by the Rabbit and of Other Hydroxylated Dibenzanthracene Derivatives", J. Am. Chem. Soc., 80, pp. 1225-1236, 1958.
Lagna, et al., "Generation and phenotypic analysis of sigma receptor type 1 (o'1) knowckout mice," European Journal of Neuroscience, 2003, vol. 18, pp. 2188-2196.
Laird, J., et al., "Deficits in visceral pain and referred hyperalgesia in Nav1.8 (SNS/PN3)-null mice", The Journal of Neuroscience, 22(19), Oct. 1, 2002, pp. 8352-8356.
Lang, M., et al., "The Use of Polymer Heteronuclei for Crystalline Polymorph selection," Journal of the American Chemical Society, 2002, vol. 124, No. 50, pp. 14834-14835, SI-S2.
Lau, et al. ( 2010) Electroacupuncture versus celecoxib for neuropathic pain in rat SNL model. Neuroscience 170 (2): 655-661.
Le Bars, D., et al., Animal models of nociception. *Pharmacal. Rev.* 2001; 53, 597-652.
Lee, S., et al., "Large-Scale Aspects of Salt Formation: Processing of Intermediates and Final Products", Handbook of Pharmaceutical Saks: Properties, Selection, and use. 2002, Chapter 8, pp. 191-192, 211-214, Chapter 12, 265-266, 282-283.
Li, et al., "Asymmetric Total Synthesis and Formal Total Synthesis of the Antitumor Sesquiterpenoid (+)-Eremantholide A", Organic Letters, vol. 9, No. 7, pp. 1267-1270, 2007.
Li, et al., "Synthesis and Structure-Antitumor Activity of 4,6-Diamino-1,2-Dihydro-2,2-Dirmethyi-1-(Substituted Naphthyi-2)-1,3,5-Triazines", Chem. Res. Chinese Univ., 7(3), pp. 197-200, 1991.
Li, F., et al., "Taurine reverses neurological and neurovascular deficits in Zucker diabetic fatty rats," Neurobiology of Disease, vol. 22, 2006, pp. 669-676.
Lippincott's Illustrated Review: Pharmacology, Richard Harvey, 5th, edition published by Wolters Kluwer "Gastrointestinal and Antiemetic Drugs", pp. 351-362.
Lowry, et al., "Protein measurement with the folin phenol reagent," J. Bio. Chem, 1951, vol. 193, pp. 265-275.
Luger N.M., et al., "Efficacy of systemic morphine suggests a fundarnen tai difference in the mechanisms that generate bone cancer vs. inflammatory pain", Pain 2002, vol. 99, pp. 397-406.
Lugar, N.M., et al., "Bone Cancer Pain: From Model to Mechanism to Therapy", J. Pain and Symp. Manag. 2005, vol. 29 pp. 832-846.
Luedtke, R. R. et al., "Neuroprotective effects of high affinity Sigma 1receptor selective compounds," Brain Res. Mar. 2, 2012; 1441:17-26.
Mantyh, "Bone cancer pain; From mechanism to therapy", Opin. Support. Palliat. Care, 2014, vol. 8, pp. 83-90.
Mar. 1, 2016 Fourth Office Action, issued in connection with Chinese Patent Application No. 201180065232.X, including English language translation.
Mar. 29, 2016 Office Action, issued in connection with Japanese Patent Application No. 2013-541369, including English translation.
Marks, D.M., et al., "Serotonin-Norepinephrine reuptake inhibitors for pain control: Premise and promise", Current Neuropharmacology, 2009, 7, pp. 331-336.
Maryanoff, B.E., et al., The Wittig Olefination Reaction and Modifications Involving Phosphoryl-Stabilized Carbanions. Stereochemistry, Mechanism, and Selected Synthetic Aspectsu, Chem. Rev., 1989, vol. 89, pp. 863-927.
Matsumoto RR1, Pouw B. Correlation between neuroleptic binding to sigma(1) and sigma(2) receptors and acute dystonic reactions. Eur J. Phamacol. Aug. 4, 2000; 401(2):155-60.

(56) References Cited

OTHER PUBLICATIONS

Maurice, T., Su, T. P., The pharmacology of Sigma-1 receptors. *Pharmacal. Ther.* 2009; 124, 195-206.

McGill, J.B., et al., "I3-Biocker use and diabetes symptom score: results from the Gemini study", Diabetes, Obesity and Metabolism, vol. 9, No. 3, May 2007, pp. 408-417.

Mega, et al., Experimental Diabetes Research, Jan. 12, 2011, Diabetic Nephropathy Amelioration by a Low-Dose Sitaglipton in an Animal Model of Type 2 Diabetes (Zucker Diabetic Fatty Rat).

Menten, J., "Co-analgesics and adjuvant medication in opioid treated cancer pain", Eur. J. Cancer Supplement 2005, vol. 3, pp. 77-86.

Mielke, s. et al., "Peripheral neuropathy: A persisting challenge in paclitaxel-based regimes" / European Journal of Cancer, 2006, vol. 42, pp. 24-30.

Ming, L.C., "Screening Polymorphic Forms of Drug Substances by Using Generalized Ming,• Crystallization Techniques," May 2007 (English language Translation of Abstract).

Moncada A., et al., Effects of serine/threonine protein phosphatase inhibitors on morphine-induced antinociception in the tail flick test in mice. *Eur J Pharmacal.* Mar. 28, 2003; 465(1-2): 53-60.

Mosandl, et al., "Stereoisomeric Flavor Compounds XLIV: Enantioselective Analysis of Some Important Flavor Molecules", J. High Resol. Chromatog 13(9), pp. 660-662, 1990.

Mouedden, et al., "Pharmacological evaluation of opioid and non-opioid analgesics in a murine bone cancer model of pain", Pharm. Biochem. and Behavior, 2007, vol. 86, pp. 458-467.

Mueller, et al., "Some Derivatives of 7-Methoxy- and 10-Methoxybenzo (f) quinoline", J. Am. Chem. Soc., 66, pp. 860-862, 1944.

Mukerji, et al., "Addition of Nitrile Oxides to Olefins, Synthesis of Dihydrojasmone and Starting Material for Prostanoids, A Novel Route to Pyrroles", Tetrahedron, 39 (13) pp. 2231-2235, 1983.

Nakajima K., et al., An increase in spinal cord noradrenaline is a major contributor to the antihyperalgesic effect of antidepressants after peripheral nerve injury in the rat, *Pain*, 2012; 153(5): 990.

Nakazato A., et al., "Synthesis and SAR of 1-alkyl-2-phenylethylamine derivatives designed from N,Ndipropyl-4-methoxy-3-(2-phenylethoxy) phenylethylamine to discover ?1 ligands", J. Med. Chem., (1999), vol. 42, pp. 3965-70.

Nausea and Vomiting (PDQ) Health Professional Version: Prevention and Management of Acute or Delayed Nausea and Vomiting (Emesis). National Cancer Institute. <http://www.cancer.gov/about-cancer/treatrnent/sideeffects/nausea/nausea-hp-pdq#section/—66>.

Nieto, F. R., et al., "188 A New Selective Sigma-1 Receptor Antagonist (S1RA) Inhibits the Development and Expression of Neuropathic Pain Induced by Paclitaxel in Mice," European Journal of Pain Supplements, vol. 4, No. 1, 2010, p. 56.

Nieto, F.R., et al., "Tetrodotoxin inhibits the development and expression of neuropathic pain induced by paclitaxel in mice", Pain, 2008, vol. 137, pp. 520-531.

Niiyama, et al., "SB366791, a TRPVI antagonist, potentiates analgesic effects of systemic morphine in a murine model of bone cancer pain", Br. J. Anaesth 2009, vol. 102, pp. 251-258,.

O'Brien, C. J., "Recycling the Waste: The Development of a Catalytic Witting Reaction", Agnew. Chem. Int. Ed. 2009, vol. 48, pp. 6836-6839.

Office Action dated Mar. 18, 2013 in connection with Russian Patent Application No. 2010138634, filed Feb. 17, 2009.

Official Action corresponding to Japanese Patent Application No. 2013-523580, dated Mar. 31, 2015.

Ohsawa, et al., "Effect of acute topical application of(+)-pentazocine on the mechanical allodynia in diabetic mice" Eur. J. P'harmacal., 2010, 641, pp, 49-53.

Olivar, T., et al.. "Cyclophosphamide cystitis in mice: behavioural characterisation and correlation with bladder inflammation", European Journal of Pain, 3, 1999, pp. 141-149.

Oltman, C.L., et al., "Progression of vascular and neural dysfunction in sciatic nerves of Zucker diabetic fatty and Zucker rats", Am. J. Physiol. Endocrinol. Metab., vol. 289, 2005, pp. E113- E122.

Oltman, C.L., et al., "Vascular and neural dysfunction in Zucker diabetic fatty rats: a difficult condition to reverse", Diabetes, Obesity and Metabolism, vol. 10, 2008, pp. 64-74.

Oltman, et al., Treatment of Zucker diabetic fatty rats with AVE7688 improves vascular and neural dysfunction, Diabetes, Obesity and Metabolism, vol. 11, No. 3, 2009, pp. 223-233.

O'Neill, J., et al., Unravelling the mystery of capsaicin: a tool to understand and treat pain. Pharmacol Rev. Oct. 2012; 64(4):939-71.

Ongioco, C. D., et al., Alpha2-adrenergic receptors in human dorsal root ganglia: predominance of alpha2b and alpha2c subtype mRNSs, *Anesthesiology* 2000; 92 (4): 968-976.

Otto, et al., Pain Medicine, 2011, 12: 437-450, "Longitudinal Study of painful Diabetic Neuropathy in the Zucker Diabetic Fatty Rat Model of Type 2 Diabetes: Impaired Basal G-Protein Activity Appears to Underpin Marked Morphine Hyposensitivity at 6 Months,".

Owens, N. J. et al., "Antiemetic efficacy of prochlorperazine, haloperidol, and droperidol in cisplatin-induced emesis", Clinical Pharmacy, 1984, vol. 3, pp. 168-170.

Pacharinsak, C., et al., "Animal Models of Cancer Pain", Comparative Medicine, 2008, vol. 58, No. 3, pp. 220-233.

Paice, J. A., "Clinical Challenges: Chemotherapy-induced Peripheral Neuropathy", Seminars in Oncology Nursing, 2009, vol. 25, N. 2, Suppl 1, pp. S8-S19.

Palmer, J. L., and Fisch, M. J., "Association Between Symptoms Distress and Survival in Outpatients Seen in a Palliative Care Caner Center", Journal of Pain and Symptom Management, 2005, vol. 29, No. 6, pp. 565-571.

Paquette et al. in Psychopharmacology (Berlin) 204(4):743-754 (2009).

Park, S.B. et al. "Mechanisms Underlying Chemotherapy-Induced Neurotoxicity and the Potential for Neuroprotective Strategies", Current Medicinal Chemistry, 2008, vol. 15, pp. 3081-3094.

Perret, D., et al., "Targeting voltage-gated calcium channels for neuropathic pain management", Neurotherapeutics: The Journal of the American Society for Experimental NeuroTherapeutics, vol. 6, Oct. 2009, pp. 679-692.

Petrie, C. et al., "A Novel Biotinylated Menylate Analogue Derived from Pyrazolou3,4-D 3/4 Pyrimidine for Labeling DNA Probes "Bioconjugate Chemistry, ACS, Washington, DD, US LNKD—DOI:10.1021/BC00012A011, vol. 2, No. 6, Nov. 1, 1991 (Nov. 1, 1991), pp. 441-446, XP0005727891SSN: 1043-1802.

Polomano, R.C., et al., "Chemotherapy-evoked Painful Peripheral Neuropathy", Pain Medicine, 2001, vol. 2, No. 1, pp. 8-14.

Polomano, R.C., et al., "Pain and neuropathy in cancer survivors: Surgery, radiation, and chemotherapy can cause pain; research could improve its detection and treatment", Cancer Nursing, Lippincott-Raven Pub., Hagerstown, MD, US, (Mar. 1, 2006), vol. 29, No. 2, suppl, ISSN 0162-220X, pp. 39-47, XP009107315 [A] 1-16.

Poncelet, A.N., "Risk factors, patterns of presentation, diagnosis, and treatment", Geriatrics, vol. 58, No. 6, Jun. 2003, pp. 16-18, 24-30.

Postma, T.J., et al., "Paclitaxel-induced neuropathy," Annals of Oncology, 1995, vol. 6, pp. 489-494.

Price, et al., J. Am. Chem. Soc., (2005), vol. 127, p. 5512.

Prodrug [online], [retrieved on Mar. 11, 2007. Retrieved from the Internet, URL; http://en.wikipedia.org/wiki/Prodrug>.

Puente, B., et al., "Sigma-1 receptors regulate activity-21 induced spinal sensitization and neuropathic pain after peripheral nerve injury", Pain, 2009, vol. 145, pp. 294-303.

Puskas, F., et al., Intrathecal clonidine and severe hypotension after cardiopulmonary bypass, *Anesth Analg.* 2003; 97 (5): 1251-1253.

Quasthoff, S., et al., "Chemotherapy-induced peripheral neuropathy," J Neural., 2002, vol. 249, pp. 9-17.

Radesca, et al., "Synthesis and Receptor Binding of Enantimeric N-Substituted cis-N-[2(3,4 Dishlorophenyl)ethyl]-2-(1-pyrrolidinyl)cyclohexylamines as High-Affinity o'Receptor Ligands," J. Med. Chem., 1991, vol. 34, pp. 3058-3065.

Rao, R.D., et al., "Efficacy of Lamotrigine in the Management of Chemotherapy-induced Peripheral Neuropathy placebo-controlled trial, N01C3", Cancer; 2008, 112(12), 2802-2808.

Raynov, J., "Antiemetics: Side effects and reactions", Archive of Oncology, 2001, vol. 9, No. 3, pp. 151-153.

(56) References Cited

OTHER PUBLICATIONS

Receveur, Jean-Marie, et al., "Synthesis and biological evaluation of conformationally restricted gabapentin analogues", Bioorganic & Medicinal Chemistry Letters, 9, 1999, pp. 2329-2334.

Reuben, S. S., et al., "Evaluation of efficacy of the perioperative administration of venlafaxine XR in the prevention of postmastectomy pain syndrome", Journal of Pain and Symptom Management, Feb. 2004, vol. 27, No. 2, pp. 133-139.

Rodriguez-Spong, B., et al., "General principles of pharmaceutical solid polymorphism: a supramolecular Perspective," Advanced Drug Delivery Reviews, vol. 56 (2004) pp. 241-274.

Roh, D., et al., "Intrathecal Injection of the 01 Receptor Antagonist BD1047 Blocks Both Mechanical Allodynia and Increases in Spinal NR1 Expression during the Induction Phase of Rodent Neuropathic Pain", Anesthesiology, 2008, vol. 109, No. 5, pp. 879-889.

Roila, F., et al., "Delayed emesis: moderately emetogenic chemotherapy", Support Care Cancer, 2005, vol. 13, pp. 104-108.

Romero, L., et al., J. Pharmacological properties of SIRA, a new Sigma-1 receptor antagonist that inhibits neuropathic pain and activity-induced spinal sensitization, *Br. J. Pharrnacal.* 2012; doi: 10.1111/j.1476-5381.

Roos, et al., Radiotherapy and Oncology, 2003, vol. 67, pp. 207-212.

Rossiter, et al., "Copper (H)-Mediated Arylation with Aryl Boronic Adds for the N-Derivatization of Pyrazole Libraries," J. Comb. Chem., 2004, vol. 6, pp. 385-390, published on web Feb. 5, 2004.

Rouleau, A., et al., "Anti-inflammatory and antinociceptive properites of BP 2-94, a histamine H3-receptor agonist prodrug", The Journal of Pharmacology and Experimental Therapeutics, vol. 295, No. 1, 2000, pp. 219-225.

Rowinsky, E.K. et al., "Phase I and Pharmacologic Study of Paclitaxel and Cisplatin with Granulocyte Colony-25 Stimulating Factor: Neuromuscular Toxicity is Dose-Limiting", Journal of Clinical Oncology, 1993, vol, 11, No. 10, pp. 2010-2020.

Rowinsky, E.K., et al., "Clinical Toxicities Encountered 24 with Paclitaxel (TAXOL)", Seminars in Oncolony, 1993, vol. 20, No. 4, suppl. 3, pp. 1-15.

Sabetkasaie, M., et al., "Clonidine and guanfacine-induced antinociception in visceral pain: possible role of alpha2/12 binding sites", European Journal of Pharmacology, Elsevier Scence, NL, (Oct. 6, 2004), vol. 501, No. 1-3, doi: 10.1016/J.EJPHAR.2004.08.010, ISSN 0014-2999, pp. 95-101.

Said, G., "Diabetic Neuropathy", Proceedings advanced studies in Medicine, vol. 1, No. 11, Dec. 2001, pp. 457-459.

Sakurada T., et al., Differential effects of intraplantar capsazepine and ruthenium red on capsaicin-induced desensitization in mice. Pharmacal Biochern Behay. Apr. 7, 2003; 5(1) 115-21.

Sampson, C., et al., "Effects of imidazoline I2 receptor ligands on acute nociception in rats." Neuroreport Jan. 25, 2012, (Jan. 25, 2012), vol. 23, No. 2, ISSN 1473-558X, pp. 73-77, XP009169909 [Y] 1-15.

Sarnsa, E., et al., Comparative assessment of the anaesthetic and analgesic effects of intramuscular and epidural clonidine in humans, *Can J Anaesth.* 1996; 43 (12): 1195-1202.

Sanchez-Fernandez, C., et al, "Potentiation of morphine-induced mechanical antinociception by sigma-1 receptor inhibition: role of peripheral sigma-1 receptors", Neuropharmacology, 70, 2013, pp. 348-358.

Sant et al., "The mast cell in interstitial cystitis: role in pathophysiology and pathogenesis, "Urology, 69, Suppl 4A, 2007, pp. 34-40.

Schwetz et al. in Brain Research 1181 (2007) 1-9.

Schiff, et al., Nature vol. 277 pp. 665-667. Publication date: Feb. 22, 1979.

Schlegel, T., et al., "Responsiveness of C-fiber nociceptors to punctate force-controlled stimuli in isolated rat skin: lack of modulation by inflammatory mediators and flurbiprofen" Neuroscience Letters, vol. 361. 2004, pp. 163-167.

Hanner et al, "Purification, molecular cloning, and expression of the mammalian sigma1-binding site," *Proc. Natl. Acad. Sci USA* vol. 93, pp. 8072-8077, Jul. 1996 Pharmacology.

Schoeffter, et al., "Functional, endogenously expressed 5-hydroxytryptamine 5-ht7 receptors in human vascular smooth muscle cells," British Journal of Pharmacology, 1996, vol. 117, pp. 993-994.

Schreiber, S., et al., "The antinociceptive effect of venlafaxine in mice is mediated through opioid and adrenergic mechanisms", Neuroscience Letters, Limerick, IE, (Jan. 1, 1999), vol. 273, doi: 10.1016/S0304-3940(99)00627-8, ISSN 0304-3940, pp. 85-88, XP003009174 [Y] 1-17.

Seigel, L.J., et al., The Control of Chemotherapy-Induced Emesis, Ann Intern Med. 1981; 95(3):352-359.

Selwood, D. L., et al. Synthesis and Biological Evaluation of Novel Pyrazoles and Indazoles as Activators of the Nitric Oxide Receptor, Soluble Guanylate Cyclase, J. Med, Chem, 2001, vol. 44, pp. 78-93.

Gotub et al., "Molecular Classification of Cancer: Class Discovery and Class Prediction by Gene Expression Monitoring," Science, 286: 531-537, 1999.

Sevcik, M.A., et al, "Jinti-NGF therapy profoundly reduces bone cancer pain and the accompanying increase in markers of peripheral and central sensitization", Pain 2005, vol. 115, pp. 128-141.

Shaw, et al., Proc. Soc. Exp. idol, Med., (1983), vol. 173, No, 1, pp. 68-75.

Shen, D.M., et al., "Versatile and Efficient Solid-Phase Syntheses of Pyrazoles and Isoxazoles", Organic Letters, 2000, vol. 2, No. 18, pp. 2789-2792.

Shimizu, I., et al., "Effects of AH-9700, (+)-pentazocine, DTG and oxybutynin on micturition in anesthetized rats with acetone-induced cystitis", Life Sciences 69, 2001, pp. 1691-1697.

Shimoyama, E., et al., Integrative Medicine you Need to know now "Cancer and Integrative MEdicine Palliative Medicine", Modern Physician, Nov. 2008, vol. 28, No. 11, pp. 1605-1607 [inc. machine English language translation].

Shu, et al., "Parameter Effects on the Thermal Reaction of Cystine and 2,5-Dimethyl-4-hydroxy-3(2H)-furanone", ACS Symposium Letters, 409, pp. 229-241, 1989.

Shvidenko, K.V., et al., "Recyclization Reactions of 2-(1-Benzoylpyrrolidin-2-Ylidene)Malononitrile", 2010, vol. 46, No. 1, pp. 56-60.

Siau, C., et al., "Dysregulation of Cellular Calcitt.rn Homeostasis in Chemotherapy-Evoked Painful Peripheral Neuropathy", *Anest:h Analg.*, 2006, 102(5), pp. 1485-1490.

Sierralta, F., et al., Alpha-Adrenoceptor and opioid receptor modulation of clonidine-induced antinociception, *Br J Pharmacal.* 1996; 119 (3): 551-554.

Silvey et al. in Journal of Clinical Oncology 6(9), 1397-1400 (1988) (Abstract).

Sims, A.A.F., "The heterogeneity of diabetic neuropathy", Frontiers in Bioscience, May 2008, pp. 4809-4816.

Sima, A.A.F., et al., "A comparison of diabetic polyneuropathy in Type II diabetic BBZDR/Wor rats and in Type I diabetic BBNVor rats", Diabetologia, vol. 43, 2000, pp. 786-793.

Smith, et al., Life Sci., (2004), vol. 74, No. 21, pp. 2593-604.

Smith, J.C. et al., "Haloperidol: An alternative butyrophenone for nausea and vomiting prophylaxis in anesthesia," AANA Journal 2005, vol. 73, No. 41 pp. 273-275.

Snyder, et al., "Receptor Mechanisms in Antipsychotic Drug Action: Focus on Sigma Receptors," Journal of Neuropsychiatry, Winter 1989, vol. No. 1, pp. 7-15.

Sonal, G., et al., Ther. Adv. Urol., (2011), vol. 3, No. 1, pp. 19-33.

Souillac, et al., Characterization of Delivery Systems, Differential Scanning Calorimetry, pp. 217-218 (in Encyclopedia of Controlled Drug Delivery, 1999, John Wiley & Sons, pp. 212-227.

Stahl, P.H., et al., "Monographs on Acids and Bases", Handbook of Pharmaceutical Salts: Properties, Selection, and Use, 2002, pp. 265-266, 282-283.

Strupp, et al., "Transdermal fentanyl during high-dose chemotherapy and autologous stem cell support" (2000) Oncology Reports, 7:659-661.

(56) References Cited

OTHER PUBLICATIONS

Stubblefield, et al., "Upper-Extremity Pain Disorders in Breast Cancer" (2006) Arch Phys Med Rehabil, vol. 87, Suppl 1, pp. S96-S99.
Su, et al., Pharmacology & Therapeutics, vol. 124, pp. 195-206, 2009.
Sussman, N., "SNRis versus SSRis: Mechanisms of action in treating depression and painful physical symptoms", Primary Care Companion J. Clin, Psychiatry, 2003, 5 (suppl 7), pp. 19-26.
Suzuki, Y., et al., "Lowered response threshold and increased responsiveness to mechanical stimulation of cutaneous nociceptive fibers in streptozotocin-diabetic rat skin in vitro—correlates of mechanical allodynia and hyperalgesia observed in the early stage of diabetes", Neuroscience Research, vol. 43, 2002, pp. 171-178.
Tanda, S., et al., "Pains Resistant to Opioids, and Countermeasures thereof~Including Peripheral Neuropathy Measures of Oxaliplatin", Pharmacy, Oct. 2007, vol. 58, No. 11, pp. 2947-2953 [inc. machine English language translation].
Taylor, C.P., "Mechanisms of analgesia by gabapentin and pregabalin-calcium channel alpha2-delta [Ca v alpha2-delta]ligands", Pain, 142, 2009, pp. 13-16.
Telleria-Diaz, et al., Pain, 2010, 148, pp. 26-35.
Theoharides, T.C., "Mast cell involvement in interstitial cystitis: a review of human experimental evidence," Urology, (2001), vol. 57, No. 6, pp. 47-55.
Tietze, L., et al., Synthesis, (11), 1079-1080, 1993.
Tramer, M. R., et al., "Efficacy and Adverse Effects of Prophylactic Anti emetics during Patient-Controlled Analgesia Therapy: A Quantitative Systematic Review, "Anesth. Analg., 1999, vol. 88, pp. 1354-1361.
Tyers at al. Oncology 49(4), 263-268 (1992) (Abstract).
Uchitel, O.D., et al., "Acute modulation of calcium currents and synaptic transmission by Gabapentinoids," Channels, 4:6, Nov./Dec. 2010, pp. 490-496.
Van De Merwe, J.P., et al., "Diagnostic criteria, classification, and nornendature for painful bladder syndrome/interstitial cystitis: an ESSIG proposal", European Urology, 53, 2008, pp. 60-67.
Van Sickle et al. Gastroenterology 121 (4), 767-774 (2001) (Abstract).
Vedejs, E., "Stereochemistry and Mechanism in the Wittig Reaction," Topics in Stereochemistry, 1994, vol. 21, pp. 1-157.
Velucci, "Heterogeneity of Chronic Pain", Clin. Drug Invest. 2012, 32 Suppl. 1, pp. 3-10.
Venturello, C., "2-Arylazo-2, 5-dimethyl-3-oxo-2, 3-dihyrdof urans, useful intermediates in the synthesis of 1-aryl-5-methyl-3-pyrazolones", Synthesis, 1979, pp. 283-287.
Venturello, C., et al., "A Novel Synthesis of Pyrazol-3-ones Form Biacetyl Dimer and Arenediazonium Salts", Journal of the Chemical Society, Perkin Transactions 1: Organic and Bio-organic Chemistry, (1972-1999), 7, 681-685, 1978.
Vileikyte, L., et al., Psychological aspects of diabetic neuropathic foot complications: an overview, Diabetes/Metabolism Research and Reviews, 2004, vol. 20 (Suppl1), pp. S13-S18.
Vinik, A., et al., Nature Clinical PracticeEndocrinology & Metabolism, (2006), vol. 2, pp. 2-13.
Vippagunta, et al., Crystalline solids, Advanced Drug Delivery Reviews, 48: 1-26, 2001.
Virmani, et al., Indian Journal of Chemistry, Section B: Organic Chemistry Including Medicinal Chemistry, vol. 17, 1979, pp. 472-477.
Virmani, V. et al., "Methyl-{3-[5-(4-nitro-phenyl)-1-phenyl-1H-pyrazol-3-yl]propyl}-amine", Database Beilstein, Beilstein Institute for Organic Chemistry, Frankfurt-Main, DE, Database accession No. 705147, XP002605613 [X] 1-3,9.
Virmani, V. et al., "Methyl-{5-[5-(4-nitro-phenyl)-1-phenyl-1H-pyrazol-3-yl]-butyl}amine", Database Beilstein, Beilstein Institute for Organic Chemistry, Frankfurt-Main, DE, Database accession No. 706821, XP002605614 [X] 1-3,9.
Virmani, V. et al., "Methyl-{5-[5-(4-nitro-phenyl)-1-phenyl-1H-pyrazol-3-yl]-pentyl}-amine", Database Beilstein, Beilstein Institute for Organic Chemistry, Frankfurt-Main, DE, Database accession No. 710983, XP002605615 [X] 1-3,9.
Vorobeychik, et al., "Combination Therapy for Neuropathic Pain—A Review of Current Evidence," CNS Drugs, 2011, pp. 1-12.
Wagaw, S. et al., "A Palladium-Catalyzed Strategy for the Preparation of Indoles: A Novel Entry Into the Fischer Indole Synthesis", J. American Chemical Society, 1998, vol. 120, pp. 6621- 6622.
Walker, et al., "Sigma Receptors: Biology and Function," Pharmacological Review, 1990, vol. 42, No. 4, pp. 355-402.
Wantuch, C., et al., "Pharmacological validation of a model of cystitis pain in the mouse", Neuroscience Letters, 421. 2007, pp. 250-252.
Wasserheit, C., et al., "Phase II trial of paclitaxel and cisplatin in women with advanced breast cancer: an active regimen with limiting neurotoxicity", Journal of Clinical Oncology, 1996, vol. 14, No. 7 pp. 1993-1999.
Weetman, A.P., "Graves' hyperthyroidism: how long should antithyroid drug therapy be continued to achieve remission?," Nature Clinical Practice Endocrinology and Metabolism, vol. 2, No. 1, Jan. 2006, pp. 2-3.
Werling, L.L. et al., "A comparison of the binding profiles of dextromethorphan, memantine, fluoxotinc and amitriptyline: treatment of involuntary emotional expression disorder," Exp Neurol. Oct. 2007; 207 (2):248-57.
Wickham, "Chemotherapy-Induced Peripheral Neuropathy: A Review and Implications for Oncology Nursing Practice" (2007) Clinical Journal of Oncology Nursing, vol. 11, No. 3, pp. 361-376.
Wild, S., et al., "Global Prevalence of Diabetes", Diabetes Care, vol. 27, No. 5, May 2004, pp. 1047-1053.
Wilkes, G. "Peripheral Neuropathy Related to Chemotherapy", Seminars in Oncology Nursing, 2007, vol. 23, 3. pp. 162-173.
Wilson, S. G., "The heritability of antinociception: common pharmacogenetic mediation of five neurochemically distinct analgesics," J Pharmacal Exp Ther. 2003; 304 (2): 547-559.
Winkler, et al., "Synthesis of Highly Functionalized Furanones via Aldol Reaction of 3- Silylonrfurans", Organic Letters, vol. 7, No. 3, pp. 387-389, 2005.
Wolf, S., et al., "Chemotherapy-induced peripheral neuropathy: Prevention and treatment strategies," European Journal of Cancer, 2008, vol. 44, issue 11, pp. 1507-1515.
Wu, et al., Regulatory Perspectives of Type II Prodrug Development and Time- Dependent Toxicity Management: Nonclinical Pharm/Tox Analysis and the Role of Comparative Toxicology, Toxicology, 236: 1-6, 2007.
Wunsch, et al., Journal Med. Chem. vol. 55, No. 19, pp. 8209-8210, 2012.
Xiaoping, et al., "Involvement of the spinal NMDA receptor/PKCy signaling 12 pathway in the development of bone cancer pain", Brain Research, 2010, vol. 1335, pp. 83-90.
Xu, J. et al., Identification of the PGRMCI protein complex as the putativP. sigma-2 receptor binding site. Nat Comnun, Jul. 5, 2011; 2:380.
Yaksh, T. L., Pharmacology of spinal adrenergic systems which modulate spinal nociceptive processing. *Pharmacal Biochem Behav*, 1985; 22(5): 845-58.
Yeretzian, et al., "Analysing the headspace of coffee by proton-transfer-reaction mass-spectrornetry", Int J. Mass Spect, 223-224 (1-3), pp. 115-139, 2003.
Zhang et al. in Synapse 15(4):276-284 (1993), Abstract.
Zheng, F.Y., et al. "The Response of Spinal Microglia to Chemotherapy Evoked Painful Peripheral Neuropathies Is Distinct From That Evoked by Traumatic Nerve Injuries," *Neuroscience*, 2011, 176, pp. 447-454.
Noda et al., "A Neuroactive Steroid, Dehydroepiandrosterone Sulfate, Attenuates The Development of Morphine Dependence: An Association with Sigmal Receptors," Neuroscience 2001 Abstract, Presentation No. 668.4, Nov. 2001.

\* cited by examiner

SIGMA LIGANDS FOR POTENTIATING THE ANALGESIC EFFECT OF OPIOIDS AND OPIATES IN POST-OPERATIVE PAIN AND ATTENUATING THE DEPENDENCY THEREOF

RELATED APPLICATIONS

This application is a §371 national stage of PCT International Application No. PCT/EP2011/051644, Feb. 4, 2011, claiming priority of Eurpoean Patent Application No. EP 10 382 023.9, filed Feb. 4, 2010, the contents of each of which are hereby incorporated by reference into this application.

FIELD OF THE INVENTION

The present invention relates to use of sigma receptor ligands for potentiating the analgesic effect of opioids and opiates and for decreasing the dependence thereof and to a combination of a sigma ligand and opioids or opiates for use in the treatment of pain. In particular, the present invention refers to the potentiation of opioid and opiate analgesia in relation to the treatment and/or prevention of post-operative pain.

BACKGROUND

The treatment of pain conditions is of great importance in medicine. There is currently a world-wide need for additional pain therapy. The pressing requirement for a specific treatment of pain conditions is documented in the large number of scientific works that have appeared recently in the field of applied analgesics.

PAIN is defined by the International Association for the Study of Pain (IASP) as "an unpleasant sensory and emotional experience associated with actual or potential tissue damage, or described in terms of such damage" (IASP, Classification of chronic pain, $2^{nd}$ Edition, IASP Press (2002), 210). Although it is a complex process influenced by both physiological and psychological factors and is always subjective, its causes or syndromes can be classified. Some of the most relevant pain subtypes are neuropathic pain, allodynia, hyperalgesia, and peripheral neuropathy.

Over twenty million patients have surgical procedures each year. Postsurgical pain (interchangeably termed, post-incisional pain), or pain that occurs after surgery or traumatic injury, is a serious and often intractable medical problem. Pain is usually localized within the vicinity of the surgical site. Post-surgical pain can have two clinically important aspects, namely resting pain, or pain that occurs when the patient is not moving and mechanical pain which is exacerbated by movement (coughing/sneezing, getting out of bed, physiotherapy, etc.). The major problem with post-surgical pain management for major surgery is that the drugs currently used have a variety of prominent side effects that delay recovery, prolong hospitalization and subject certain vulnerable patient groups to the risk of serious complications.

The three major classes of pharmaceutical drugs used to treat post-surgical pain are the opioid analgesics, local anaesthetics, and the non-steroidal anti-inflammatory drugs (NSAID). Two of these classes of drugs, the opioid analgesics and NSAIDs, are typically administered systemically while the local anaesthetics (e.g. channel blockers) are administered non-systemically during surgery.

The systemic administration of drugs to relieve pain after surgery is frequently inadequate. For example, systemic administration of opioids after surgery may cause nausea, the inhibition of bowel function, urinary retention, inhibition of pulmonary function, cardiovascular effects, and sedation.

"Post-surgical pain" is interchangeable with "post-incisional" or "posttraumatic pain" and refers to pain arising or resulting from an external trauma such as a cut, puncture, incision, tear, or wound into tissue of an individual (including those that arise from all surgical procedures, whether invasive or non-invasive), i.e. to pain developed as a consequence of surgery. As used herein, "post-surgical pain" does not include pain that occurs without an external physical trauma. In some embodiments, post-surgical pain is internal or external pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods, e.g., with protocols well-known in the art. Post-surgical pain, as used herein, includes allodynia (i.e., pain due to a stimulus that does not normally provoke pain) and hyperalgesia (i.e., increased response to a stimulus that is normally painful), which can in turn, be thermal or mechanical (tactile) in nature. Therefore, the pain is characterized by thermal sensitivity, mechanical sensitivity and/or resting pain (e.g. persistent pain in the absence of external stimuli). Further, the pain can be primary (e.g., resulting directly from the pain-causing event) or secondary pain (e.g., pain associated with, but not directly resulting, from the pain-causing event).

Different animal models and studies on postoperative incisional pain the same are reported in the state of the art (T. J. Brennan et al. Pain 1996, 64, 493-501; P. K. Zahn et al. Regional Anaesthesia and Pain Medicine 2002, Vol. 27, No 5 (September-October), 514-516).

Opioids and opiates are potent analgesics widely used in clinical practice. Opioid and opiates drugs are classified typically by their binding selectivity in respect of the cellular and differentiated tissue receptors to which specific drug specie binds as a ligand. These receptors include mu (μ), delta (δ), kappa (κ) and the nociceptive receptors.

The well-known narcotic opiates, such as morphine and its analogs, are selective for the opioid mu receptors. Mu receptors mediate analgesia, respiratory depression, and inhibition of gastrointestinal transit. Kappa receptors mediate analgesia and sedation. However, despite their good activity as analgesics, opioids and opiates have the drawback of causing dependence.

Sigma receptors are non-opiaceous type of receptors of great interest in pharmacology due to their role in analgesia related processes. The sigma binding sites have preferential affinity for the dextrorotatory isomers of certain opiate benzomorphans, such as (+)SKF 10047, (+)cyclazocine, and (+)pentazocine and also for some narcoleptics such as haloperidol. The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

It has been reported that some sigma ligands in combination with opioids or opiates are capable of modulating the analgesic effect thereof. It is known, for example, that haloperidol potentiates the activity of different opioids and opiates such as morphine, DADL or bremazocine [Chichenkov, O. N. et al: Effect of haloperidol on the analgesic activity of intracisternally and intrathecally injected opiate agonists, Farmakologiya i Toksikologiya (Moscow) (1985), 48(4), 58-61]. Chien C. et al. also referred the synergistic effect of the combination of haloperidol and morphine [Selective antagonism of opioid analgesia by a sigma system, J Pharmacol Exp Ther (1994), 271, 1583-1590 and Sigma antagonists potentiate opioid analgesia in rats, Neurosci Lett (1995), 190, 137-139] and Marazzo A. et al taught the capacity of the sigma ligand (+)-MR200 to modulate K-opioid receptor mediated analgesia. Mei J. et al confirmed the importance of sigma-1 receptors as a modulatory system on the analgesic activity of opioid drugs [Sigma1 receptor modulation of opioid analgesia in the mouse, J Pharmacol Exp Ther (2002), 300(3), 1070-1074]. Notwithstanding, in all of this cases the problem of dependence induced by opioids and opiates remain to be present.

One of the pharmacological approaches to solve the problem of opioid and opiate dependence has been the co-administration of opioids or opiates and sigma ligands. For instance, sigma-1 receptor agonist SA4503 has been shown to have a modulatory effect on addiction to morphine [Nomura, M. et al: Studies on drug dependence (Rept. 322): Attenuation of morphine- and psychostimulants-induced place preference by sigma1 receptor agonist SA4503, 72nd Annual Meeting of the Japanese Pharmacological Society (Sapporo, Japan-March 1999)]. Also, sigma-1 agonist DHEA has shown some capacity to attenuate the development of morphine dependence [Noda, Y. et al: A neuroactive steroid, dehydroepiandrosterone sulfate, attenuates the development of morphine dependence: an association with sigma1 receptors, 31st Annual Meeting of the Society of Neuroscience (San Diego-November 2001)]. EP1130018 teaches the use of sigma ligands for the treatment of drug addiction to morphine, cocaine and methamphetamine. However, none of these approaches show an enhancement of the analgesic effect of morphine.

Therefore, there is a need to provide new treatments for post-surgical pain which reduce side effects shown by known drugs.

BRIEF DESCRIPTION OF THE INVENTION

The inventors of the present invention have found and demonstrated that the administration of some specific sigma receptor ligands in conjunction with an opioid or opiate may surprisingly potentiate synergistically the analgesic effects of the latter, while decreasing their associated dependence.

Therefore, one aspect of the present invention relates to a combination for simultaneous, separate or sequential administration comprising at least one sigma ligand of formula (I), or a pharmaceutically acceptable salt, isomer, prodrug or solvate thereof, and at least one opioid or opiate, for use in the prevention and/or treatment of pain developed as a consequence of surgery

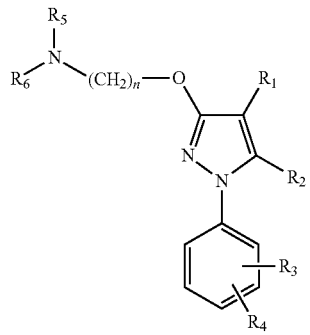

(I)

wherein, $R_1$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen;

$R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen;

$R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen, or together they form an optionally substituted fused ring system;

$R_5$ and $R_6$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_8$, —$NR_8C(O)R_8$, —$NO_2$, —N=$CR_8R_8$, or halogen;

or together form, with the nitrogen atom to which they are attached, a substituted or unsubstituted, aromatic or non-aromatic heterocyclyl group;

n is selected from 1, 2, 3, 4, 5, 6, 7 or 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted, aromatic or non-aromatic heterocyclyl, substituted or unsubstituted alkoxy, substituted or unsubstituted aryloxy, or halogen.

A further aspect of the invention refers to the sigma ligand of formula (I) as defined above, or a pharmaceutically acceptable salt, isomer, prodrug or solvate thereof, for use in potentiating the analgesic effects of an opioid or opiate and/or attenuating dependency thereof when said opioid or opiate is used in the prevention and/or treatment of pain developed as a consequence of surgery.

A further aspect of the invention refers to the sigma ligand of formula (I) as defined above, or a pharmaceutically acceptable salt, isomer, prodrug or solvate thereof, for use in potentiating the analgesic effects of an opioid or opiate when said opioid or opiate is used in the prevention and/or treatment of pain developed as a consequence of surgery.

A further aspect of the invention refers to the sigma ligand of formula (I) as defined above, or a pharmaceutically acceptable salt, isomer, prodrug or solvate thereof, for use in attenuating dependency of an opioid or opiate when said opioid or opiate is used in the prevention and/or treatment of pain developed as a consequence of surgery.

Another aspect of this invention refers to the use of the combination, for simultaneous, separate or sequential administration, comprising at least one sigma ligand of formula (I) as defined above, or a pharmaceutically acceptable salt, isomer, prodrug or solvate thereof, and at least one opioid or opiate for manufacturing a medicament for the prevention and/or treatment of pain developed as a consequence of surgery.

Another aspect of this invention refers to the use of a sigma ligand of formula (I) as defined above, or a pharmaceutically acceptable salt, isomer, prodrug or solvate thereof for manufacturing a medicament for potentiating the analgesic effects of an opioid or opiate and/or attenuating dependency thereof in relation to the prevention and/or treatment of pain developed as a consequence of surgery.

Another aspect of the invention is a method of treatment of a patient suffering from pain developed as a consequence of surgery, or likely to suffer pain as a result of a surgical treatment, which comprises administering to the patient in need of such a treatment or prophylaxis a therapeutically effective amount of a combination comprising at least sigma ligand of formula (I) as defined above, or a pharmaceutically acceptable salt, isomer, prodrug or solvate thereof, and an opioid or opiate.

These aspects and preferred embodiments thereof are additionally also defined in the claims.

DETAILED DESCRIPTION OF THE INVENTION

Figure 1:
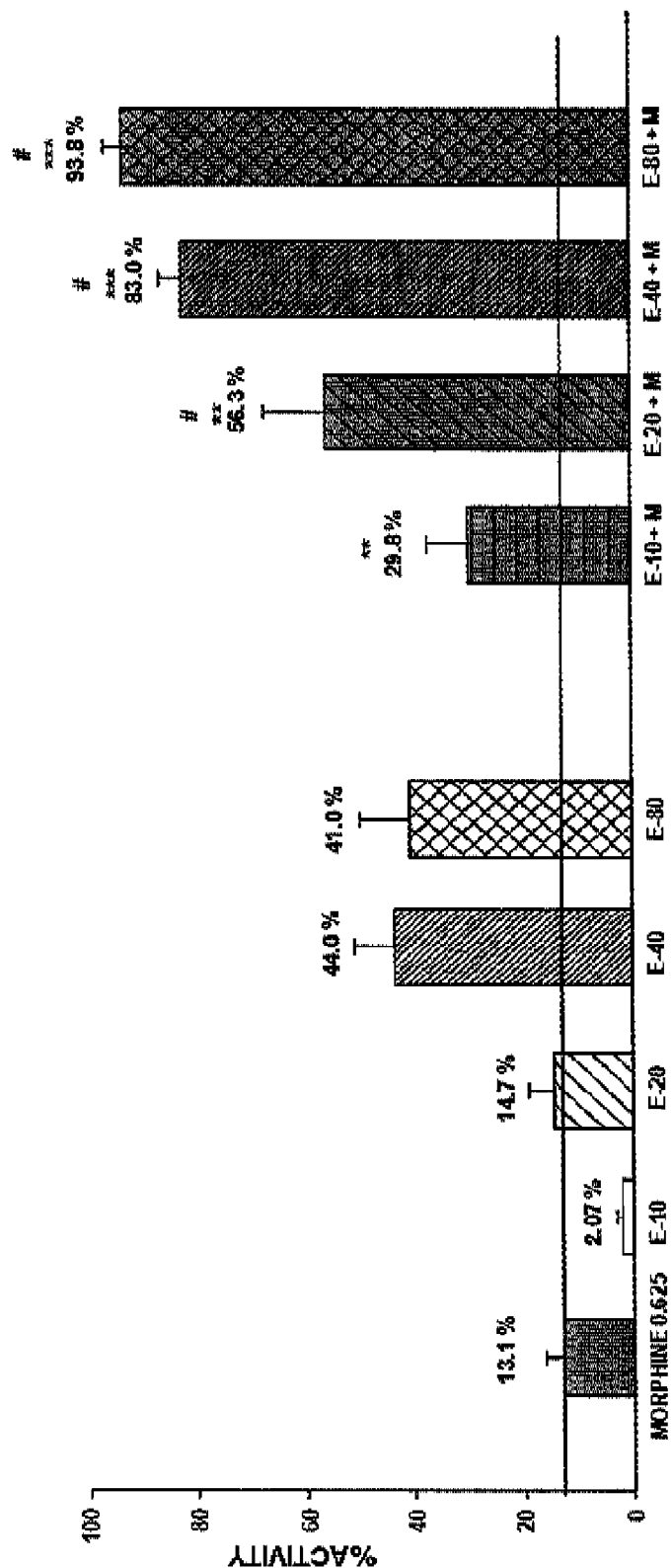
FIG. 1: Potentiation of morphine analgesia (0.625 mg/kg) by compound 63 (10, 20, 40 and 80 mg/kg) in a mechanical allodynia rat model. n=10, #: $p<0.05$; ns: $p>0.05$ Dunnett, compound 63+M vs. Morphine; : $p<0.01$; *: $p>0.001$ t-Student, compound 63+M vs. compound 63.

In the context of the present invention, the following terms have the meaning detailed below.

"Alkyl" refers to a straight or branched hydrocarbon chain radical consisting of carbon and hydrogen atoms, containing no unsaturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. If substituted by aryl we have an "alkylaryl" radical, such as benzyl and phenethyl. If substituted by heterocyclyl we have an "heterocyclylalkyl" radical.

"Alkenyl" refers to an alkyl radical having at least 2 C atoms and having one or more unsaturated bonds. In a particular embodiment the alkenyl group has two to eight carbon atoms. In a particular embodiment, the alkenyl group is vinyl, 1-methyl-ethenyl, 1-propenyl, 2-propenyl, or butenyl.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term"cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3 to 15 membered ring radical which consists of carbon atoms and from one to five heteroatoms selected from the group consisting of nitrogen, oxygen, and sulfur, preferably a 4 to 8 membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —OR$_a$ where R$_a$ is an alkyl radical as defined above, e.g., methoxy, ethoxy, propoxy, etc. Analogously, "aryloxy" refers to a radical of the formula —OR$_c$ where R$_c$ is an aryl radical as defined above, e.g., phenoxy.

"Amino" refers to a radical of the formula —NH$_2$, —NHR$_a$ or —NR$_a$R$_b$, optionally quaternized. In an embodiment of the invention each of R$_a$ and R$_b$ is independently selected from an alkyl radical as defined above.

"Halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

"Opioids" and "opiates" refer to compounds that bind to opioid receptors. Compounds that bind to the opioid receptor within the scope of the present invention include natural opiates, such as morphine, codeine and thebaine; semi-synthetic opiates, derived from the natural opioids, such as hydromorphone, hydrocodone, oxycodone, oxymorphone, desomorphine, diacetylmorphine, nicomorphine, dipropanoylmorphine, benzylmorphine and ethylmorphine; fully synthetic opioids, such as sufentanil, remifentanil, fentanyl, pethidine, methadone, tapentadol, tramadol and propoxyphene; and endogenous opioid peptides, produced naturally in the body, such as endorphins, enkephalins, dynorphins, and endomorphins and their analogs.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are preferred particularly, as well as those formed with ammonium cations (NH$_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of the sigma ligand of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

Any compound referred to herein is intended to represent such specific compound as well as certain variations or forms. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The sigma ligands of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As used herein, the terms "treat", "treating" and "treatment" include the eradication, removal, reversion, alleviation, modification, or control of pain induced by a surgical operation, after the pain onset.

As used herein, the terms "prevention", "preventing", "preventive" "prevent" and "prophylaxis" refer to the capacity of a therapeutic to avoid, minimize or difficult the onset or development of a disease or condition before its onset, in this case pain induced by a surgical operation.

Therefore, by "treating" or "treatment" and/or "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as pain. As such, the method of the present invention also includes situations where the condition is completely inhibited, e.g., prevented from happening, or stopped, e.g., terminated, such that the subject no longer experiences the condition. As such, the present method includes both preventing and managing pain induced by a surgical operation, particularly, peripheral neuropathic pain, allodynia, causalgia, hyperalgesia, hyperesthesia, hyperpathia, neuralgia, neuritis or neuropathy.

As used herein, the term "potentiating the analgesic effect of an opioid or opiate" refer to the increase in the affectivity of the analgesic effect of said opioids or opiates produced by sigma ligands of formula (I). In an embodiment of the invention said potentiating effect induces an increase in the analgesic effect of opioids by a factor of 1.2, 1.5, 2, 3, 4 or more, even in some case by a factor of 14 or 15, when compared, with the opioids or opiates, or with the sigma ligand of formula (I) when administered in isolation. The measurement can be done following any known method in the art. In an embodiment of the invention, the sigma ligand of formula (I) potentiates the analgesic effect of an opioid or opiate by a factor of at least 1.2 when measured in a mechanical allodynia rat model or in a in a thermal hyperalgesia rat model. In a further embodiment, said factor is of at least 1.5, 2, 3, 4 or more, even in some case by a factor of 14 or 15.

As used herein, the term "decreasing the dependency induced by an opioid or opiate" refer to the amelioration, decrease or reduction of the dependency of the patient from said opioids or opiates produced by sigma ligands of formula (I). In an embodiment of the invention said decreasing effect induces a reduction in the dependency from opioids by a factor of 1.2, 1.5, 2, 3, 4 or more, even in some case by a factor of 14 or 15, when compared, with the opioids or opiates when administered in isolation. The measurement can be done following any known method in the art. In an embodiment of the invention, the sigma ligand of formula (I) reduces the dependency of the patient from said opioid or opiate by a factor of at least 1.2 when measured with the place conditioning paradigm model. In a further embodiment, said factor is of at least 1.5, 2, 3, 4 or more, even in some case by a factor of 14 or 15.

In a preferred embodiment, $R_1$ in the compounds of formula (I) is selected from H, —$COR_8$, and substituted or unsubstituted alkyl. More preferably, $R_1$ is selected from H, methyl and acetyl. A more preferred embodiment is when $R_1$ is H.

In another preferred embodiment, $R_2$ in the compounds of formula (I) represents H or alkyl, more preferably methyl.

In yet another preferred embodiment of the invention, $R_3$ and $R_4$ in the compounds of formula (I) are situated in the meta and para positions of the phenyl group, and preferably, they are selected independently from halogen and substituted or unsubstituted alkyl.

In an especially preferred embodiment of the invention, in the compounds of formula (I) both $R_3$ and $R_4$ together with the phenyl group form an optionally substituted fused ring system (for example, a substituted or unsubstituted aryl group or a substituted or unsubstituted, aromatic or non-aromatic heterocyclyl group may be fused), more preferably, a naphthyl ring system.

Also in the compounds of formula (I), embodiments where n is selected from 2, 3, 4 are preferred in the context of the present invention, more preferably n is 2.

Finally, in another embodiment it is preferred in the compounds of formula (I) that $R_5$ and $R_6$ are, each independently, $C_{1-6}$alkyl, or together with the nitrogen atom to which they are attached form a substituted or unsubstituted heterocyclyl group a, in particular a group chosen among morpholinyl, piperidinyl, and pyrrolidinyl group. More preferably, $R_5$ and $R_6$ together form a morpholine-4-yl group.

In preferred variants of the invention, the sigma ligand of formula (I) is selected from:

[1] 4-{2-(1-(3,4-dichlorophenyl)-5-methyl-1H pyrazol-3-yloxy)ethyl} morpholine,
[2] 2-[1-(3,4-Dichlorophenyl)-5-methyl-1H-pyrazol-3-yloxy]-N,N-diethylethanamine,
[3] 1-(3,4-Dichlorophenyl)-5-methyl-3-[2-(pyrrolidin-1-yl)ethoxy]-1H-pyrazole,
[4] 1-(3,4-Dichlorophenyl)-5-methyl-3-[3-(pyrrolidin-1-yl)propoxy]-1H-pyrazole,
[5] 1-{2-[1-(3,4-Dichlorophenyl)-5-methyl-1H-pyrazol-3-yloxy]ethyl}piperidine,
[6] 1-{2-[1-(3,4-Dichlorophenyl)-5-methyl-1H-pyrazol-3-yloxy]ethyl}-1H-imidazole,
[7] 3-{1-[2-(1-(3,4-Dichlorophenyl)-5-methyl-1H-pyrazol-3-yloxy)ethyl]piperidin-4-yl}-3H-imidazo[4,5-b]pyridine,
[8] 1-{2-[1-(3,4-Dichlorophenyl)-5-methyl-1H-pyrazol-3-yloxy]ethyl}-4-methylpiperazine,
[9] Ethyl 4-{2-[1-(3,4-dichlorophenyl)-5-methyl-1H-pyrazol-3-yloxy]ethyl}piperazine carboxylate,
[10] 1-(4-(2-(1-(3,4-dichlorophenyl)-5-methyl-1H-pyrazol-3-yloxy)ethyl)piperazin-1-yl)ethanone,
[11] 4-{2-[1-(4-Methoxyphenyl)-5-methyl-1H-pyrazol-3-yloxy]ethyl}morpholine,
[12] 1-(4-Methoxyphenyl)-5-methyl-3-[2-(pyrrolidin-1-yl)ethoxy]-1H-pyrazole,
[13] 1-(4-Methoxyphenyl)-5-methyl-3-[3-(pyrrolidin-1-yl)propoxy]-1H-pyrazole,
[14] 1-[2-(1-(4-Methoxyphenyl)-5-methyl-1H-pyrazol-3-yloxy)ethyl]piperidine,
[15] 1-{2-[1-(4-Methoxyphenyl)-5-methyl-1H-pyrazol-3-yloxy]ethyl}-1H-imidazole,
[16] 4-{2-[1-(3,4-Dichlorophenyl)-5-phenyl-1H-pyrazol-3-yloxy]ethyl}morpholine,
[17] 1-(3,4-Dichlorophenyl)-5-phenyl-3-[2-(pyrrolidin-1-yl)ethoxy]-1H-pyrazole,
[18] 1-(3,4-Dichlorophenyl)-5-phenyl-3-[3-(pyrrolidin-1-yl)propoxy]-1H-pyrazole,
[19] 1-{2-[1-(3,4-Dichlorophenyl)-5-phenyl-1H-pyrazol-3-yloxy]ethyl}piperidine,
[20] 1-{2-[1-(3,4-Dichlorophenyl)-5-phenyl-1H-pyrazol-3-yloxy]ethyl}-1H-imidazole,
[21] 2-{2-[1-(3,4-Dichlorophenyl)-5-phenyl-1H-pyrazol-3-yloxy]ethyl}-1,2,3,4-tetrahydroisoquinoline,
[22] 4-{4-[1-(3,4-Dichlorophenyl)-5-methyl-1H-pyrazol-3-yloxy]butyl}morpholine,
[23] 1-(3,4-Dichlorophenyl)-5-methyl-3-[4-(pyrrolidin-1-yl)butoxy]-1H-pyrazole,
[24] 1-{4-[1-(3,4-dichlorophenyl)-5-methyl-1H-pyrazol-3-yloxy]butyl}piperidine,
[25] 1-{4-[1-(3,4-Dichlorophenyl)-5-methyl-1H-pyrazol-3-yloxy]butyl}-4-methylpiperazine,
[26] 1-{4-[1-(3,4-Dichlorophenyl)-5-methyl-1H-pyrazol-3-yloxy]butyl}-1H-imidazole,
[27] 4-[1-(3,4-Dichlorophenyl)-5-methyl-1H-pyrazol-3-yloxy]-N,N-diethylbutan-1-amine,
[28] 1-{4-[1-(3,4-dichlorophenyl)-5-methyl-1H-pyrazol-3-yloxy]butyl}-4-phenylpiperidine,
[29] 1-{4-[1-(3,4-dichlorophenyl)-5-methyl-1H-pyrazol-3-yloxy]butyl}-6,7-dihydro-1H-indol-4(5H)-one,
[30] 2-{4-[1-(3,4-dichlorophenyl)-5-methyl-1H-pyrazol-3-yloxy]butyl}-1,2,3,4-tetrahydroisoquinoline,
[31] 4-{2-[1-(3,4-dichlorophenyl)-5-isopropyl-1H-pyrazol-3-yloxy]ethyl}morpholine,
[32] 2-[1-(3,4-Dichlorophenyl)-5-isopropyl-1H-pyrazol-3-yloxy]-N,N-diethylethanamine,
[33] 1-(3,4-Dichlorophenyl)-5-isopropyl-3-[(pyrrolidin-1-yl)ethoxy]-1H-pyrazole,
[34] 1-(3,4-Dichlorophenyl)-5-isopropyl-3-[3-(pyrrolidin-1-yl)propoxy]-1H-pyrazole,
[35] 1-{2-[1-(3,4-Dichlorophenyl)-5-isopropyl-1H-pyrazol-3-yloxy]ethyl}piperidine,
[36] 2-{2-[1-(3,4-Dichlorophenyl)-5-isopropyl-1H-pyrazol-3-yloxy]ethyl}-1,2,3,4-tetrahydroisoquinoline,
[37] 4-{2-[1-(3,4-dichlorophenyl)-1H-pyrazol-3-yloxy]ethyl}morpholine,
[38] 2-[1-(3,4-dichlorophenyl)-1H-pyrazol-3-yloxy] N,N-diethylethanamine,
[39] 1-(3,4-dichlorophenyl)-3-[2-(pyrrolidin-1-yl)ethoxy]-1H-pyrazole,
[40] 1-{2-[1-(3,4-dichlorophenyl)-1H-pyrazol-3-yloxy]ethyl}piperidine,
[41] 1-(3,4-dichlorophenyl)-3-[3-(pyrrolidin-1-yl)propoxy]-1H-pyrazole,
[42] 1-{2-[1-(3,4-Dichlorophenyl)-5-methyl-1H-pyrazol-3-yloxy]ethyl}piperazine,
[43] 1-{2-[1-(3,4-Dichlorophenyl)-5-methyl-1H-pyrazol-3-yloxy]ethyl}pyrrolidin-3-amine,
[44] 4-{2-[1-(3,4-Dichlorophenyl)-4,5-dimethyl-1H-pyrazol-3-yloxy]ethyl}morpholine,
[46] 2-[1-(3,4-Dichlorophenyl)-4,5-dimethyl-1H-pyrazol-3-yloxy]-N,N-diethylethanamine,
[47] 1-(3,4-Dichlorophenyl)-4,5-dimethyl-3-[2-(pyrrolidin-1-yl)ethoxy]-1H-pyrazole,
[48] 1-(3,4-Dichlorophenyl)-4,5-dimethyl-3-[3-(pyrrolidin-1-yl)propoxy]-1H-pyrazole,
[49] 1-{2-[1-(3,4-Dichlorophenyl)-4,5-dimethyl-1H-pyrazol-3-yloxy]ethyl}piperidine,
[50] 4-{4-[1-(3,4-dichlorophenyl)-1H-pyrazol-3-yloxy]butyl}morpholine,
[51] (2S,6R)-4-{4-[1-(3,4-dichlorophenyl)-1H-pyrazol-3-yloxy]butyl}-2,6-dimethylmorpholine,
[52] 1-{4-[1-(3,4-dichlorophenyl)-1H-pyrazol-3-yloxy]butyl}piperidine,
[53] 1-(3,4-Dichlorophenyl)-3-[4-(pyrrolidin-1-yl)butoxy]-1H-pyrazole,
[55] 4-[1-(3,4-dichlorophenyl)-1H-pyrazol-3-yloxy]-N,N-diethylbutan-1-amine,
[56] N-benzyl-4-[1-(3,4-dichlorophenyl)-1H-pyrazol-3-yloxy]-N-methylbutan-1-amine,
[57] 4-[1-(3,4-dichlorophenyl)-1H-pyrazol-3-yloxy]-N-(2-methoxyethyl)-N-methylbutan-1-amine,
[58] 4-{4-[1-(3,4-dichlorophenyl)-1H-pyrazol-3-yloxy]butyl}thiomorpholine,
[59] 1-[1-(3,4-Dichlorophenyl)-5-methyl-3-(2-morpholinoethoxy)-1H-pyrazol-4-yl]ethanone,
[60] 1-{1-(3,4-dichlorophenyl)-5-methyl-3-[2-(pyrrolidin-1-yl)ethoxy]-1H-pyrazol-4-yl}ethanone,
[61] 1-{1-(3,4-dichlorophenyl)-5-methyl-3-[2-(piperidin-1-yl)ethoxy]-1H-pyrazol-4-yl}ethanone,
[62] 1-{1-(3,4-dichlorophenyl)-3-[2-(diethylamino)ethoxy]-5-methyl-1H-pyrazol-4-yl}ethanone,
[63] 4-{2-[5-Methyl-1-(naphthalen-2-yl)-1H-pyrazol-3-yloxy]ethyl}morpholine,
[64] N,N-Diethyl-2-[5-methyl-1-(naphthalen-2-yl)-1H-pyrazol-3-yloxy]ethanamine,
[65] 1-{2-[5-Methyl-1-(naphthalen-2-yl)-1H-pyrazol-3-yloxy]ethyl}piperidine,

[66] 5-Methyl-1-(naphthalen-2-yl)-3-[2-(pyrrolidin-1-yl) ethoxy]-1H-pyrazole and its pharmaceutically acceptable salts, solvates or prodrug thereof is performed.

In a preferred variant of the invention, the sigma ligand of formula (I) is 4-{2-[5-Methyl-1-(naphthalen-2-yl)-1H-pyrazol-3-yloxy]ethyl}morpholine or a salt thereof.

Preferably, the compound of formula I used is 4-{2-[5-Methyl-1-(naphthalen-2-yl)-1H-pyrazol-3-yloxy]ethyl}morpholine hydrochloride.

These particular compounds are designated in the examples of the present invention as compounds 63 (and a salt thereof).

A preferred embodiment of the present invention comprises the use of a combination of 4-{2-[5-Methyl-1-(naphthalen-2-yl)-1H-pyrazol-3-yloxy]ethyl}morpholine hydrochloride and an opioid or opiate selected from the group consisting of morphine, tramadol, sufentanil, remifentanil, fentanyl, tapentadol, oxycodone, and buprenorphine. In a preferred embodiment of the present invention, the opiate utilized is morphine or its analogs. In another preferred embodiment of the present invention, the opioid utilized is tramadol or its analogs. In another preferred embodiment of the present invention, the opioid utilized is sufentanil or its analogs. In another preferred embodiment of the present invention, the opioid utilized is remifentanil or its analogs. In another preferred embodiment of the present invention, the opioid utilized is fentanyl or its analogs. In another preferred embodiment of the present invention, the opioid utilized is tapentadol or its analogs. In another preferred embodiment of the present invention, the opioid utilized is oxycodone or its analogs. In another preferred embodiment of the present invention, the opioid utilized is buprenorphine or its analogs.

Analogs of these opioids or opiates are known to the skilled person and refer in general to any compound structurally derived from them including their pharmaceutically acceptable salts, isomers, prodrugs or solvates. Thus, a "morphine analog" may be any compound structurally derived from morphine as, for instance, those disclosed in EP0975648. Particular analogs of morphine include hydromorphone, dihydromorphine, oxymorphone, desomorphine, diacetylmorphine, nicomorphine, dipropanoylmorphine, benzylmorphine and ethylmorphine.

The compounds of formula (I) and their salts or solvates can be prepared as disclosed in the previous application WO2006/021462.

The present invention refers also to the use of pharmaceutical compositions comprising the sigma ligands of formula (I) as defined above, or a pharmaceutically acceptable salt, isomer, prodrug or solvate thereof, and opioids or opiates combined jointly or separately with at least a pharmaceutically acceptable carrier, additive, adjuvant or vehicle.

The auxiliary materials or additives can be selected among carriers, excipients, support materials, lubricants, fillers, solvents, diluents, colorants, flavor conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition used according to the present invention can be adapted to any form of administration, be it orally or parenterally, for example pulmonarily, nasally, rectally and/or intravenously. Therefore, the formulation according to the present invention may be adapted for topical or systemic application, particularly for dermal, subcutaneous, intramuscular, intra-articular, intraperitoneal, pulmonary, buccal, sublingual, nasal, percutaneous, vaginal, oral or parenteral application. The preferred form of rectal application is by means of suppositories.

Suitable preparations for oral applications are tablets, pills, chewing gums, capsules, granules, drops or syrups. Suitable preparations for parenteral applications are solutions, suspensions, reconstitutable dry preparations or sprays.

The combination of the invention may be formulated as deposits in dissolved form or in patches, for percutaneous application. Skin applications include ointments, gels, creams, lotions, suspensions or emulsions.

Having described the present invention in general terms, it will be more easily understood by reference to the following examples which are presented as an illustration and are not intended to limit the present invention.

The combination of the invention may be formulated for its simultaneous, separate or sequential administration, with at least a pharmaceutically acceptable carrier, additive, adjuvant or vehicle. This has the implication that the combination of the sigma ligand of formula (I) and the opioid or opiate may be administered:

a) As a combination that is being part of the same medicament formulation, both being then administered always simultaneously.

b) As a combination of two units, each with one of them giving rise to the possibility of simultaneous, sequential or separate administration. In a particular embodiment, the sigma ligand of formula (I) is independently administered from the opioid or opiate (i.e in two units) but at the same time. In another particular embodiment, the sigma ligand of formula (I) is administered first, and then the opioid or opiate is separately or sequentially administered. In yet another particular embodiment, the opioid or opiate is administered first, and then the sigma ligand of formula (I) is administered, separately or sequentially, as defined.

In a particular embodiment of the present invention, the pain developed as a consequence of surgery is peripheral neuropathic pain, allodynia, causalgia, hyperalgesia, hyperesthesia, hyperpathia, neuralgia, neuritis or neuropathy. More preferably, the pain is hyperalgesia or mechanical allodynia.

"Neuropathic pain" is defined by the IASP as "pain initiated or caused by a primary lesion or dysfunction in the nervous system" (IASP, Classification of chronic pain, $2^{nd}$ Edition, IASP Press (2002), 210). For the purpose of this invention this term is to be treated as synonymous to "Neurogenic Pain" which is defined by the IASP as "pain initiated or caused by a primary lesion, dysfunction or transitory perturbation in the peripheral or central nervous system". Neuropathic pain according to this invention is restricted to the neuropathic pain resulting from a surgery.

According to the IASP "peripheral neuropathic pain" is defined as "a pain initiated or caused by a primary lesion or dysfunction in the peripheral nervous system" and "peripheral neurogenic pain" is defined as "a pain initiated or caused by a primary lesion, dysfunction or transitory perturbation in the peripheral nervous system" (IASP, Classification of chronic pain, $2^{nd}$ Edition, IASP Press (2002), 213).

According to the IASP "allodynia" is defined as "a pain due to a stimulus which does not normally provoke pain" (IASP, Classification of chronic pain, $2^{nd}$ Edition, IASP Press (2002), 210).

According to the IASP "causalgia" is defined as "a syndrome of sustained burning pain, allodynia and hyperpathia after a traumatic nerve lesion, often combined with vasomotor and sudomotor dysfunction and later trophic changes" (IASP, Classification of chronic pain, 2$^{nd}$ Edition, IASP Press (2002), 210).

According to the IASP "hyperalgesia" is defined as "an increased response to a stimulus which is normally painful" (IASP, Classification of chronic pain, 2$^{nd}$ Edition, IASP Press (2002), 211).

According to the IASP "hyperesthesia" is defined as "increased sensitivity to stimulation, excluding the senses" (IASP, Classification of chronic pain, 2$^{nd}$ Edition, IASP Press (2002), 211).

According to the IASP "hyperpathia" is defined as "a painful syndrome characterized by an abnormally painful reaction to a stimulus, especially a repetitive stimulus, as well as an increased threshold" (IASP, Classification of chronic pain, 2$^{nd}$ Edition, IASP Press (2002), 212).

The IASP draws the following difference between "allodynia", "hyperalgesia" and "hyperpathia" (IASP, Classification of chronic pain, 2$^{nd}$ Edition, IASP Press (2002), 212):

| Allodynia | Lowered threshold | Stimulus and response mode differ |
|---|---|---|
| Hyperalgesia | Increased response | Stimulus and response rate are the same |
| Hyperpathia | Raised threshold Increased response | Stimulus and response rate may be the same or different |

According to the IASP "neuralgia" is defined as "pain in the distribution of a nerve or nerves" (IASP, Classification of chronic pain, 2$^{nd}$ Edition, IASP Press (2002), 212).

According to the IASP "neuritis" is defined as "inflammation of a nerve or nerves" (IASP, Classification of chronic pain, 2$^{nd}$ Edition, IASP Press (2002), 212).

According to the IASP "neuropathy/neuritis" is defined as "a disturbance of function or pathological change in a nerve: in one nerve mononeuropathy, in several nerves mononeuropthy multiplex, if diffuse and bilateral, polyneuropathy" (IASP, Classification of chronic pain, 2$^{nd}$ Edition, IASP Press (2002), 212).

In some embodiments, the post-surgical pain includes one or more of: thermally induced pain, mechanically induced pain, or resting pain. For instance, post-surgical pain can include mechanically induced pain and/or resting pain. In some cases, the post-surgical pain includes resting pain.

In certain embodiments, allodynia is suppressed, ameliorated and/or prevented, and in some embodiments, hyperalgesia is suppressed, ameliorated and/or prevented. In some instances, the pain is chronic pain. In other cases, the pain is at, proximal and/or near to one or more site(s) of external trauma, wound or incision. In certain embodiments, the combination of the sigma ligand of formula (I) and the opioid or opiate can be administered prior to an activity likely to result in external trauma, wound or incision, such as surgery. For example, the combination of the sigma ligand of formula (I) and the opioid or opiate can be administered 30 minutes, 1 hour, 2 hours, 5 hours, 10 hours, 15 hours, 24 hours or even more, such as 1 day, several days, or even a week, two weeks, three weeks, or more prior to the activity likely to result in external trauma, wound or incision, such as prior to surgery. In other embodiments, the combination of the sigma ligand of formula (I) and the opioid or opiate can be administered during and/or after surgery or activity that resulted in external trauma, wound or incision. In some instances, the combination of the sigma ligand of formula (I) and the opioid or opiate is administered 1 hour, 2 hours, 3 hours, 4 hours, 6 hours, 8 hours, 12 hours, 24 hours, 30 hours, 36 hours, or more, after surgery, or activity that resulted in external trauma, wound or incision.

In one embodiment of the invention it is preferred that the sigma ligand of formula (I) is used in therapeutically effective amounts. The physician will determine the dosage of the present therapeutic agents which will be most suitable and it will vary with the form of administration and the particular compound chosen, and furthermore, it will vary with the patient under treatment, the age and weight of the patient, the type of pain being treated, its severity. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

According to the present invention the dosage of the opioid or opiate can be reduced when combined with a sigma ligand of formula (I), and therefore attaining the same analgesic effect with a reduced dosage, and thus attenuating dependency. The sigma ligands of formula (I) may induce an increase in the analgesic effect of opioids of a factor of 1.2, 1.5, 2, 3, 4 or more, even in some case by a factor of 14 or 15. For example, in the case of the mechanical allodynia test with morphine, the increase observed with 10 mg of compound 63 was from 2.7% to 29.1% (see FIG. 1). Other dosages in the same test have reached increases from 14.7% to 56.3, 44.0% to 83.0% or 41.0% to 93.8%.

For example, the dosage regime that must be administered to the patient will depend on the patient's weight, the type of application, the condition and severity of the disease. A preferred dosage regime comprises an administration of a compound of formula I within a range of 0.5 to 100 mg/kg and of the opioid or opiate from 0.15 to 15 mg/kg. The administration may be performed once or in several occasions.

The following examples are merely illustrative of certain embodiments of the invention and cannot be considered as restricting it in any way.

EXAMPLES

Example 1

Synthesis of 4-{2-[5-Methyl-1-(naphthalen-2-yl)-1H-pyrazol-3-yloxy]ethyl}morpholine (Compound 63) and its Hydrochloride Salt

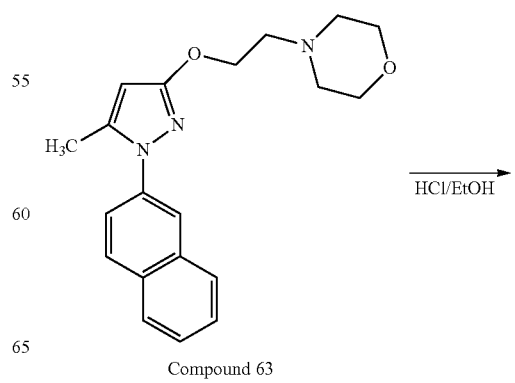

Compound 63

-continued

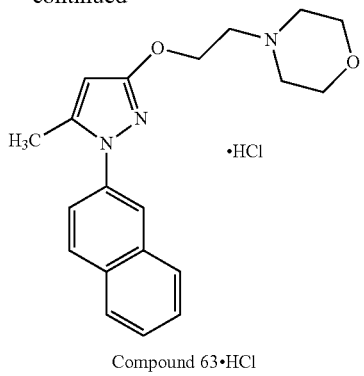

Compound 63·HCl

Compound 63 can be can be prepared as disclosed in the previous application WO2006/021462. Its hydrochloride can be obtained according the following procedure:

Compound 63 (6.39 g) was dissolved in ethanol saturated with HCl, the mixture was stirred then for some minutes and evaporated to dryness. The residue was crystallized from isopropanol. The mother liquors from the first crystallization afforded a second crystallization by concentrating. Both crystallizations taken together yielded 5.24 g (63%) of the corresponding hydrochloride salt (m.p.=197-199° C.)

$^1$H-NMR (DMSO-$d_6$) δ ppm: 10.85 (bs, 1H), 7.95 (m, 4H), 7.7 (dd, J=2.2, 8.8 Hz, 1H), 7.55 (m, 2H), 5.9 (s, 1H), 4.55 (m, 2H), 3.95 (m, 2H), 3.75 (m, 2H), 3.55-3.4 (m, 4H), 3.2 (m, 2H), 2.35 (s, 3H).

HPLC purity: 99.8%

Example 2

Assessment of Analgesic Activity Against Post-Operative Pain in Rats: Enhanced Synergistic Effect of Compound 63, Opioids and Opiate in the Treatment of Post-Operative Pain a) General Protocol for the Assessment of Analgesia in the Treatment Post-Operative Pain The induction of anaesthesia in rats was performed with 3% isofluran for veterinary use, employing an Ohmeda vaporizer and an anaesthesia chamber. Anaesthesia was kept during the surgical operation by a tube which directs the isofluran vapours to the animal's snout. Once the rats were anaesthetised, they were laid down in a prone position and their right hindpaws were cleaned out with alcohol.

Then, a skin incision in the hindpaw of about 10 mm was made by means of a scalpel, starting about 5 mm from the heel and extending toward the toes. Fascia was located and by means of curve scissors muscle was elevated and a longitudinal incision of about 5 mm was made, thus the muscle origin and insertion remained intact. Therefore, both superficial (skin) and deep (muscle) tissues and nerves were injured. The skin of the paw was stitched with a suturing stitch with breaded silk (3.0) and the wound was cleaned out with povidone.

The assessment was performed always 4 hours after the surgery (plantar incision), 30 or 60 minutes after the administration of said product. Two types of analysis were carried out:

Mechanical allodynia was tested using von Frey filaments: Animals were placed in methacrylate cylinders on an elevated surface, with metallic mesh floor perforated in order to apply the filaments. After an acclimation period of about 30 minutes within the cylinders, both hindpaws were stimulated (the injured and the non-injured paw, serving the latter as control), starting with the lowest force filament (0.4 g) and reaching a 15 g filament. The animal's response to pain was manifested by the withdrawal of the paw as a consequence of the painful stimulus caused by a filament. The pressure (force in grams) threshold eliciting the withdrawal of the paw was recorded.

The thermal hyperalgesia was tested using a Ugo Basile plantar test: Animals were placed in the methacrylate cages of said apparatus, having a crystal floor. The acclimatation period within the cages was about 10 minutes. The thermal stimulus came from a lamp moving below the crystal floor and which was applied to both paws, with a minimum interval of 1 minute between both stimulations in order to avoid learning behaviours. The rat was able to withdraw the paw freely when it feels the pain produced by the heat coming from the lamp; then it is switched off and the latency time to the withdrawal response is recorded in seconds. In order to avoid hurting the animal's paw, the lamp was automatically switched off after 32 seconds.

b) Opiate: Morphine

The efficacy of morphine and compound 63 in rats was evaluated separately as follows: 1) morphine was administered at a constant dose of 0.625 mg/kg and 2) compound 63 was administered at different doses (10, 20, 40 and 80 mg/kg). Both administrations were performed 3.5 hours after surgery.

Subsequently, the efficacy of the combined use of morphine and compound 63 was assayed at different doses of compound 63 (10, 20, 40 and 80 mg/kg), while the morphine dose remained constant (0.625 mg/kg). The administrations were performed simultaneously 3.5 hours after surgery.

Figure 2:
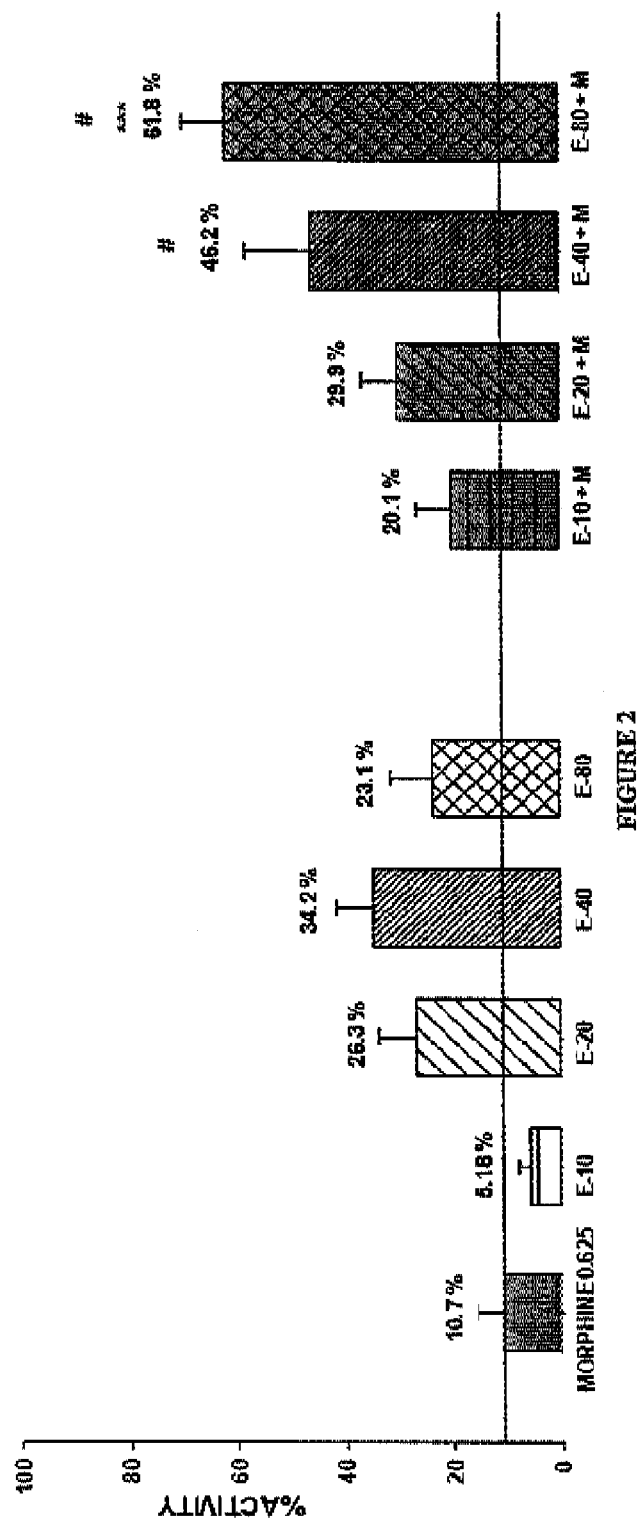
FIG. 2: Potentiation of morphine analgesia (0.625 mg/kg) by compound 63 (10, 20, 40 and 80 mg/kg) in a thermal hyperalgesia rat model. n=10, #: $p<0.05$; ns: $p>0.05$ Dunnett, compound 63+M vs. Morphine; : $p<0.01$; *: $p>0.001$ t-Student, compound 63+M vs. compound 63.
Figure 5:
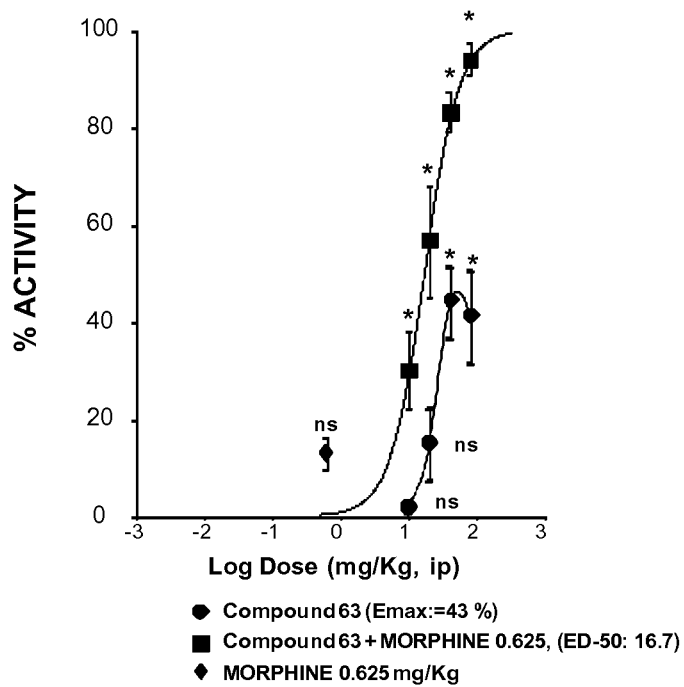
FIG. 5: Potentiation of morphine analgesia (0.625 mg/kg) by compound 63 (10, 20, 40 and 80 mg/kg) in a mechanical allodynia rat model. *: $p<0.05$ (Dunnett); ns (no significant): $p>0.05$ (Dunnett).

The treated subjects were tested according to the mechanical allodynia and thermal hyperalgesia protocols above. Compound 63 enhances morphine analgesia in the treatment of post-operative pain under both protocols. See FIGS. 1, 2 and 5.

c) Opioid: Tramadol

The efficacy of tramadol and compound 63 in rats was evaluated separately as follows: 1) tramadol was administered at a constant dose of 1.25 mg/kg and 2) compound 63 was administered at different doses (10, 20, 40, and 80 mg/kg). Both administrations were performed 3.5 hours after surgery.

Subsequently, the efficacy of the combined use of tramadol and compound 63 was assayed at different doses of compound 63 (5, 10, 20, and 40 mg/kg), while the tramadol dose remained constant (1.25 mg/kg). The administrations were performed simultaneously 3.5 hours after surgery.

Figure 3:
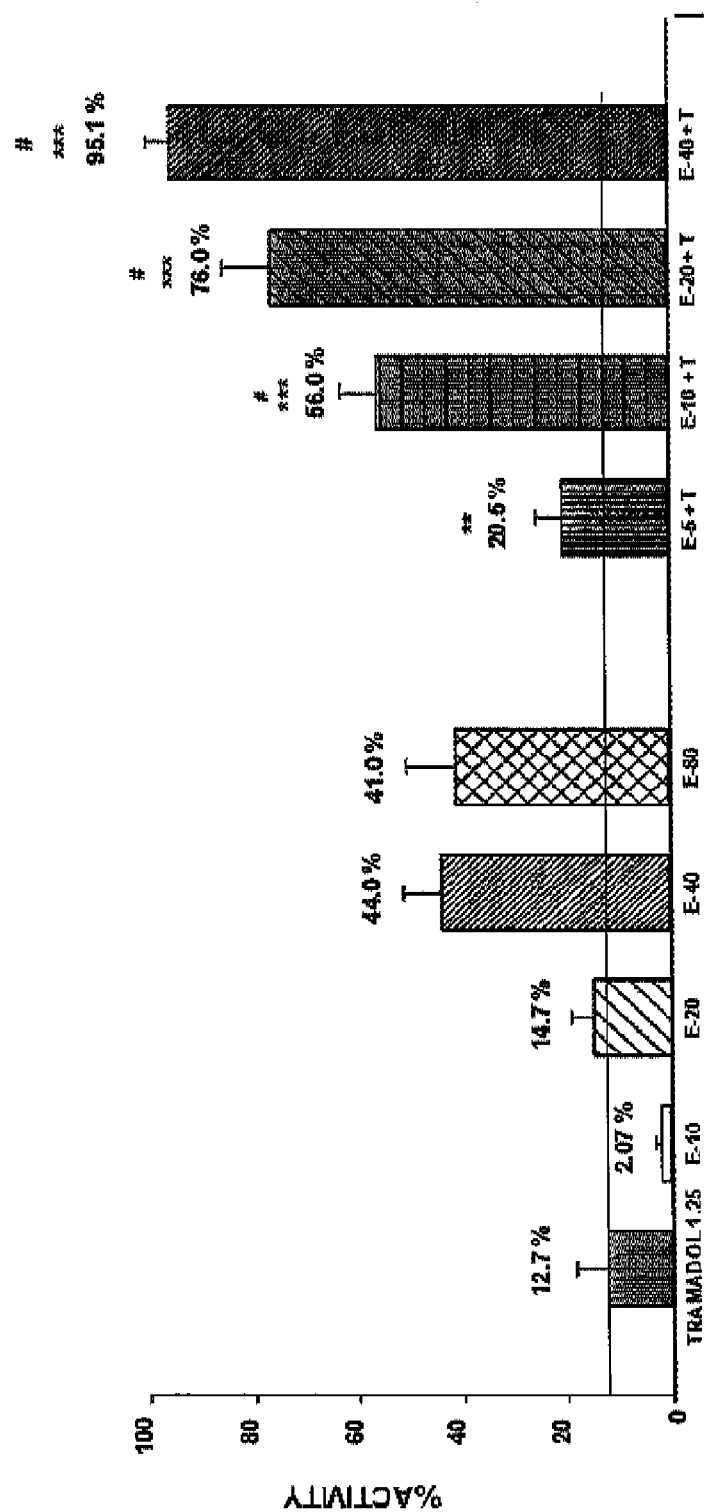
FIG. 3: Potentiation of tramadol analgesia (1.25 mg/kg) by compound 63 (5, 10, 20, and 40 mg/kg) in a mechanical allodynia rat model. n=10, #: $p<0.05$; ns: $p>0.05$ Dunnett, compound 63+T vs. Tramadol; : $p<0.01$; *: $p>0.001$ t-Student, compound 63+T vs. compound 63.
Figure 4:
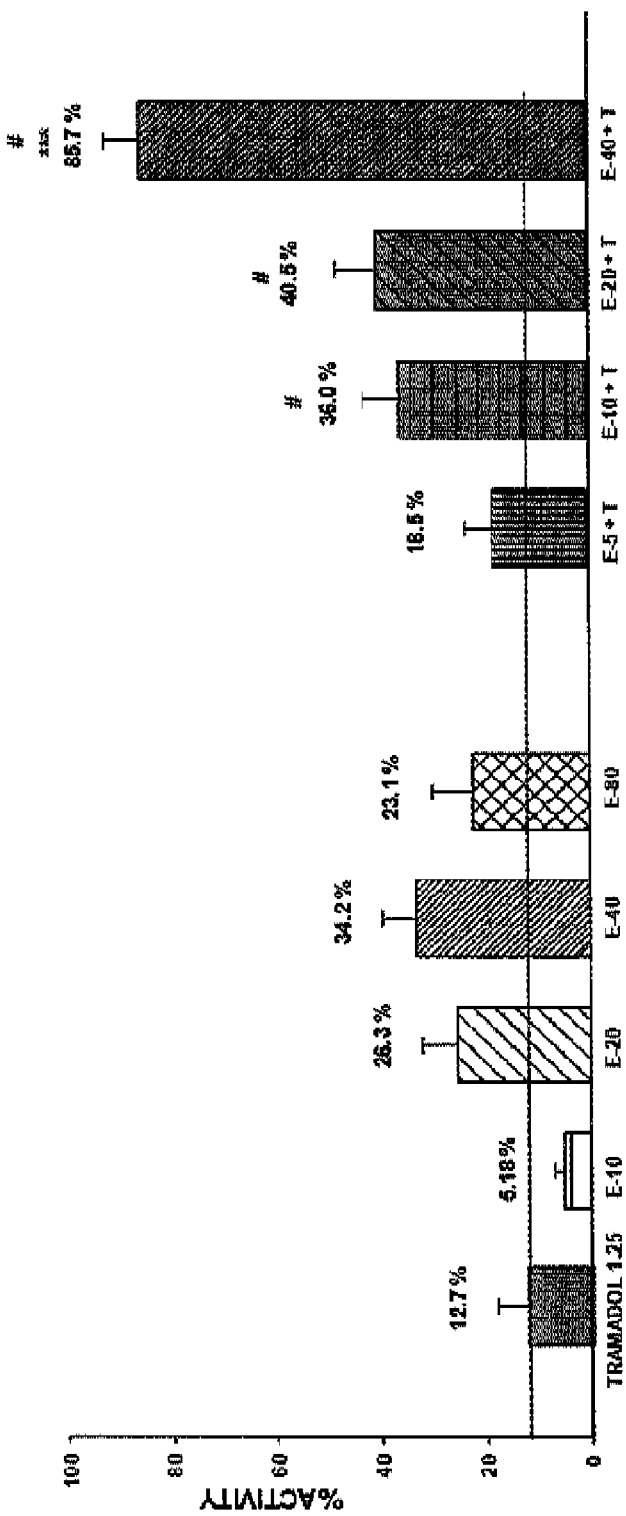
FIG. 4: Potentiation of tramadol analgesia (1.25 mg/kg) by compound 63 (5, 10, 20, and 40 mg/kg) in thermal hyperalgesia rat model. n=10, #: $p<0.05$; ns: $p>0.05$ Dunnett, compound 63+T vs. Tramadol; : $p<0.01$; *: $p>0.001$ t-Student, compound 63+T vs. compound 63.
Figure 6:
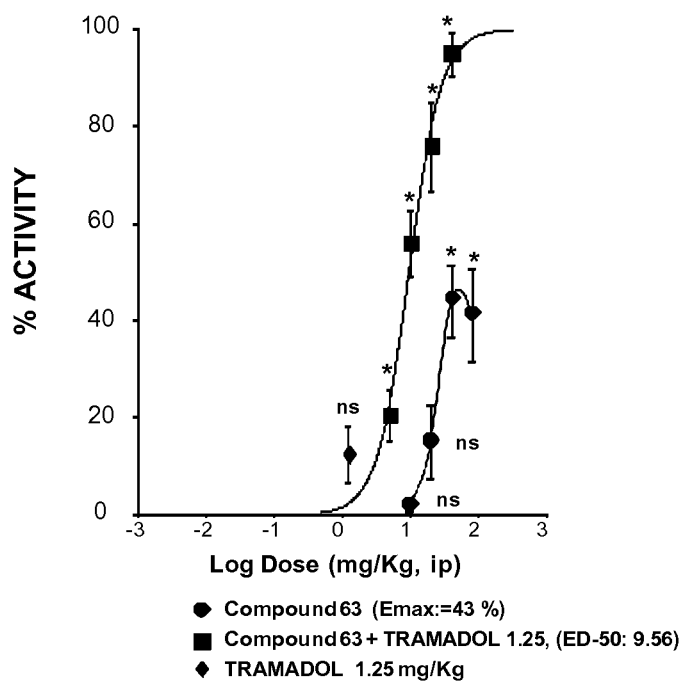
FIG. 6: Potentiation of tramadol analgesia (1.25 mg/kg) by compound 63 (5, 10, and 40 mg/kg) in a mechanical allodynia rat model. *: $p<0.05$ (Dunnett); ns (no significant): $p>0.05$ (Dunnett).

The treated subjects were tested according to the mechanical allodynia and thermal hyperalgesia protocols above. Compound 63 enhances tramadol analgesia in the treatment of post-operative pain under both protocols. See FIGS. 3, 4, and 6.

d) Opioid: Sufentanil

The efficacy of sufentanil and compound 63 in rats was evaluated separately as follows: 1) sufentanil was administered at a constant dose of 0.003 mg/kg and 2) compound 63 was administered at different doses (10, 20, 40 and 80 mg/kg). Both administrations were performed 3.5 hours after surgery.

Subsequently, the efficacy of the combined use of sufentanil and compound 63 was assayed at different doses of compound 63 (5, 10, 20 and 40 mg/kg), while the sufentanil dose remained constant (0.003 mg/kg). The administrations were performed simultaneously 3.5 hours after surgery.

Figure 7:
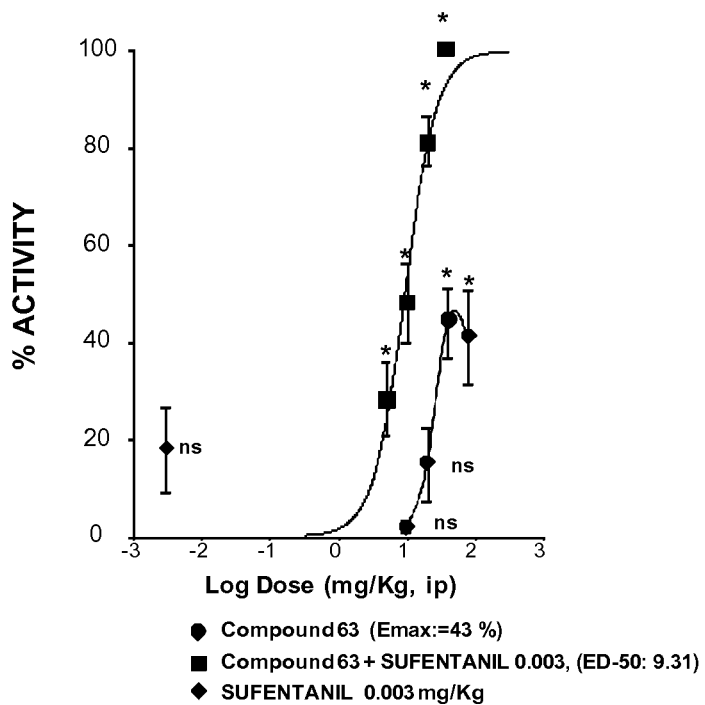
FIG. 7: Potentiation of sufentanil analgesia (0.003 mg/kg) by compound 63 (5, 10, and 40 mg/kg) in a mechanical allodynia rat model. *: $p<0.05$ (Dunnett); ns (no significant): $p>0.05$ (Dunnett).

The treated subjects were tested according to the mechanical allodynia protocol above. Compound 63 enhances sufentanil analgesia in the treatment of post-operative pain under said protocol. See FIG. 7.

e) Opioid: Remifentanil

The efficacy of remifentanil and compound 63 in rats was evaluated separately as follows: 1) remifentanil was administered at a constant dose of 0.01 mg/kg and 2) compound 63 was administered at different doses (10, 20, 40 and 80 mg/kg). Both administrations were performed 3.5 hours after surgery.

Subsequently, the efficacy of the combined use of remifentanil and compound 63 was assayed at different doses of compound 63 (2.5, 5, 10, 20, 40 and 80 mg/kg), while the remifentanil dose remained constant (0.01 mg/kg). The administrations were performed simultaneously 3.5 hours after surgery.

Figure 8:
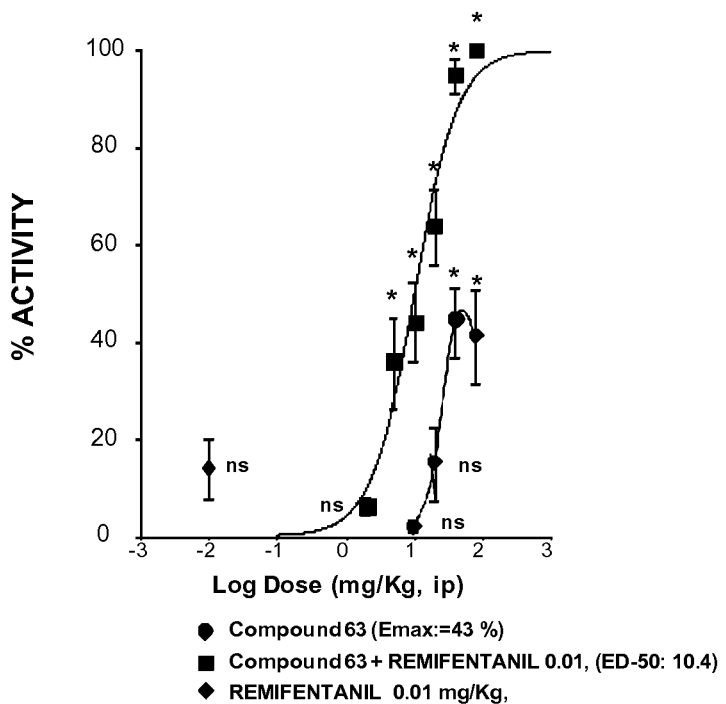
FIG. 8: Potentiation of remifentanil analgesia (0.01 mg/kg) by compound 63 (2.5, 5, 10, 20, 40 and 80 mg/kg) in a mechanical allodynia rat model. *: $p<0.05$ (Dunnett); ns (no significant): $p>0.05$ (Dunnett).

The treated subjects were tested according to the mechanical allodynia protocol above. Compound 63 enhances remifentanil analgesia in the treatment of post-operative pain under said protocol. See FIG. 8.

f) Opioid: Fentanyl

The efficacy of fentanyl and compound 63 in rats was evaluated separately as follows: 1) fentanyl was administered at a constant dose of 0.01 mg/kg and 2) compound 63 was administered at different doses (10, 20, 40 and 80 mg/kg). Both administrations were performed 3.5 hours after surgery.

Subsequently, the efficacy of the combined use of fentanyl and compound 63 was assayed at different doses of compound 63 (10, 20, 40 and 80 mg/kg), while the fentanyl dose remained constant (0.01 mg/kg). The administrations were performed simultaneously 3.5 hours after surgery.

Figure 9:
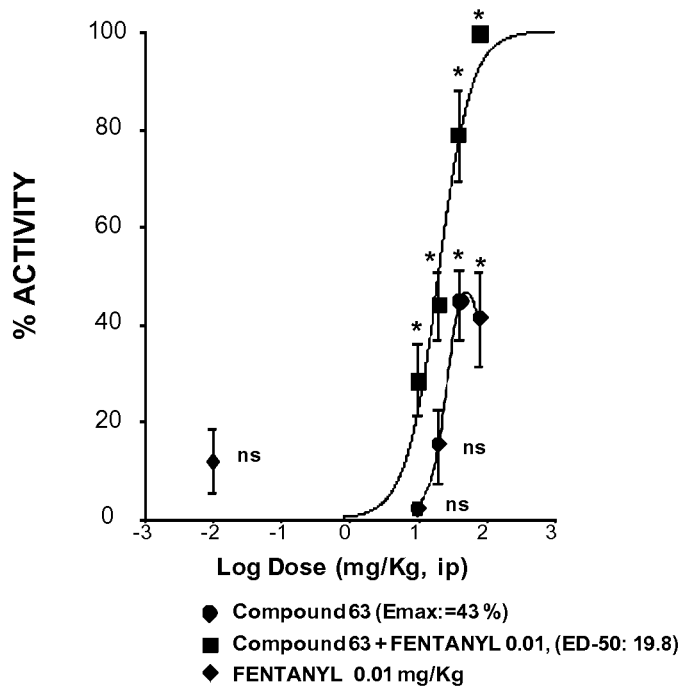
FIG. 9: Potentiation of fentanyl analgesia (0.01 mg/kg) by compound 63 (10, 20, 40 and 80 mg/kg) in a mechanical allodynia rat model. *: $p<0.05$ (Dunnett); ns (no significant): $p>0.05$ (Dunnett).

The treated subjects were tested according to the mechanical allodynia protocol above. Compound 63 enhances fentanyl analgesia in the treatment of post-operative pain under said protocol. See FIG. 9.

g) Opioid: Tapentadol

The efficacy of tapentadol and compound 63 in rats was evaluated separately as follows: 1) tapentadol was administered at a constant dose of 1.25 mg/kg and 2) compound 63 was administered at different doses (10, 20, 40 and 80 mg/kg). Both administrations were performed 3.5 hours after surgery.

Subsequently, the efficacy of the combined use of tapentadol and compound 63 was assayed at different doses of compound 63 (5, 10, 20 and 40 mg/kg), while the tapentadol dose remained constant (1.25 mg/kg). The administrations were performed simultaneously 3.5 hours after surgery.

Figure 10:
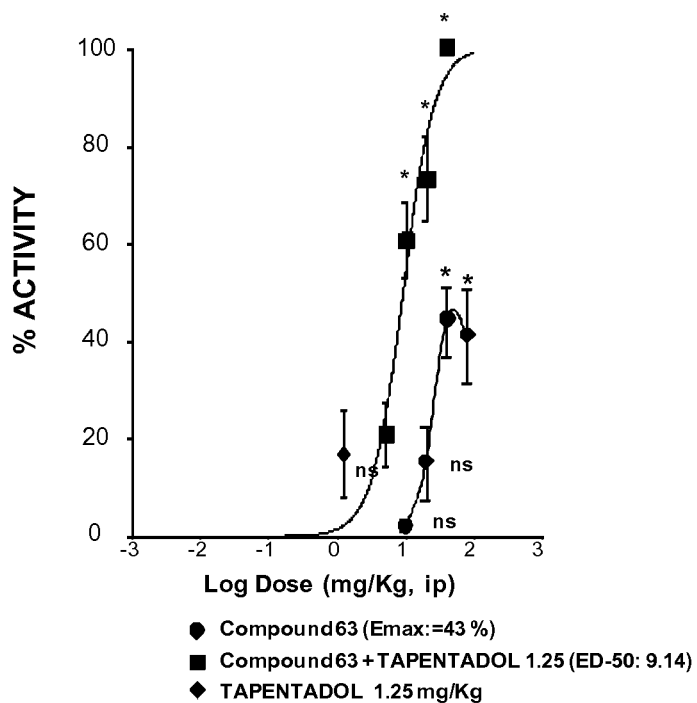
FIG. 10: Potentiation of tapentadol analgesia (1.25 mg/kg) by compound 63 (5, 10, and 40 mg/kg) in a mechanical allodynia rat model. *: $p<0.05$ (Dunnett); ns (no significant): $p>0.05$ (Dunnett).

The treated subjects were tested according to the mechanical allodynia protocol above. Compound 63 enhances tapentadol analgesia in the treatment of post-operative pain under said protocol. See FIG. 10.

h) Opioid: Oxycodone

The efficacy of oxycodone and compound 63 in rats was evaluated separately as follows: 1) oxycodone was administered at a constant dose of 0.039 mg/kg and 2) compound 63 was administered at different doses (10, 20, 40 and 80 mg/kg). Both administrations were performed 3.5 hours after surgery.

Subsequently, the efficacy of the combined use of oxycodone and compound 63 was assayed at different doses of compound 63 (2.5, 5, 10, 20 and 40 mg/kg), while the oxycodone dose remained constant (0.039 mg/kg). The administrations were performed simultaneously 3.5 hours after surgery.

Figure 11:
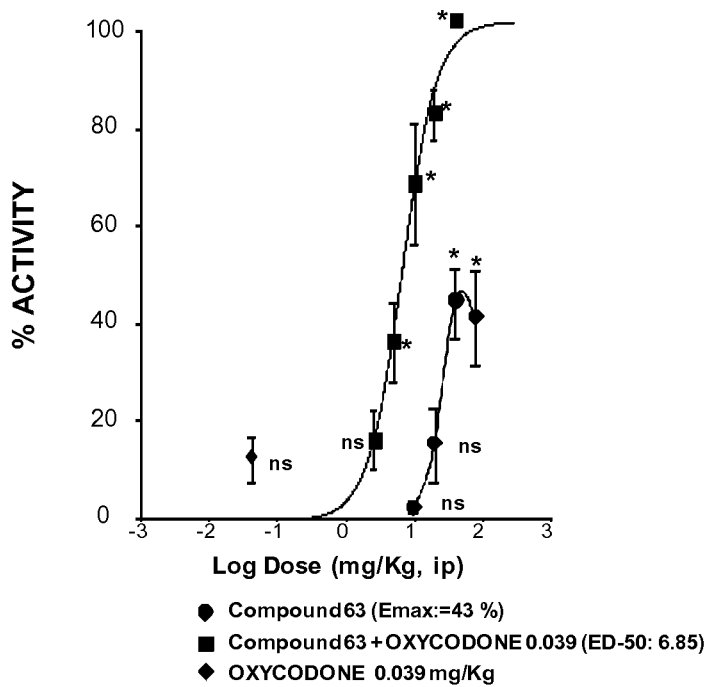
FIG. 11: Potentiation of oxycodone analgesia (0.039 mg/kg) by compound 63 (2.5, 5, 10, 20 and 40 mg/kg) in a mechanical allodynia rat model. *: $p<0.05$ (Dunnett); ns (no significant): $p>0.05$ (Dunnett).

The treated subjects were tested according to the mechanical allodynia protocol above. Compound 63 enhances oxycodone analgesia in the treatment of post-operative pain under said protocol. See FIG. 11.

i) Opioid: Buprenorphine

The efficacy of buprenorphine and compound 63 in rats was evaluated separately as follows: 1) buprenorphine was administered at a constant dose of 0.0015 mg/kg and 2) compound 63 was administered at different doses (10, 20, 40 and 80 mg/kg). Both administrations were performed 3.5 hours after surgery.

Subsequently, the efficacy of the combined use of buprenorphine and compound 63 was assayed at different doses of compound 63 (5, 10, 20 and 40 mg/kg), while the buprenorphine dose remained constant (0.0015 mg/kg). The administrations were performed simultaneously 3.5 hours after surgery.

Figure 12:
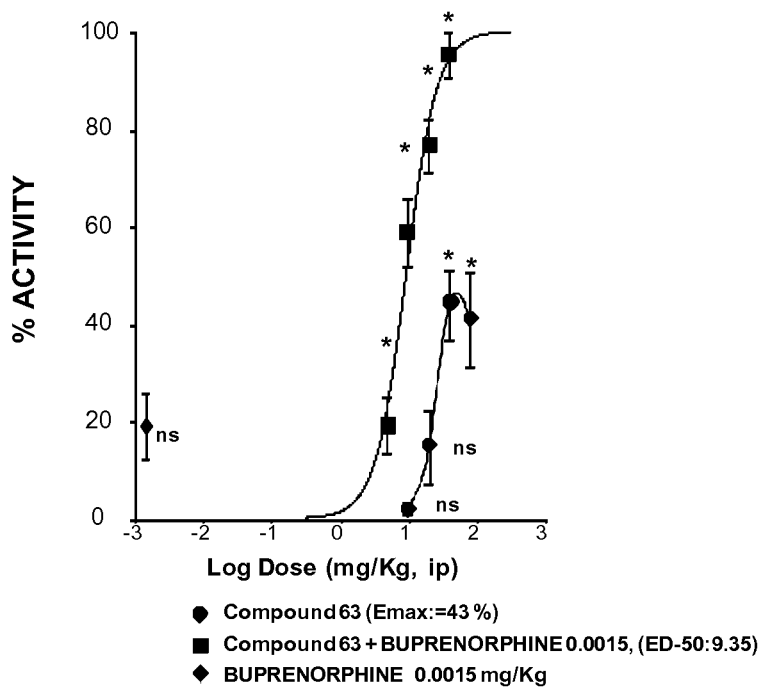
FIG. 12: Potentiation of buprenorphine analgesia (0.0015 mg/kg) by compound 63 (5, 10, 20 and 40 mg/kg) in a mechanical allodynia rat model. *: $p<0.05$ (Dunnett); ns (no significant): $p>0.05$ (Dunnett).

The treated subjects were tested according to the mechanical allodynia protocol above. Compound 63 enhances buprenorphine analgesia in the treatment of post-operative pain under said protocol. See FIG. 12.

The invention claimed is:

1. A method of treatment of a patient suffering from pain developed as a consequence of surgery, or a patient likely to suffer pain as a result of a surgical treatment, which comprises administering to the patient an amount of:
  i) an opioid or opiate selected from the group consisting of morphine, tramadol, sufentanil, remifentanil, fentanyl, tapentadol, oxycodone, and buprenorphine, and
  ii) 4-{2-[5-methyl-1-(naphthalen-2-yl)-1H-pyrazol-3-yloxy]ethyl}morpholine or a pharmaceutically acceptable salt, isomer or solvate thereof, which amounts in combination are effective to treat the pain of the patient.

2. The method according to claim 1 comprising administering a therapeutically effective amount of 4-{2-[5-methyl-1-(naphthalen-2-yl)-1H-pyrazol-3-yloxy] ethyl}morpholine hydrochloride.

3. The method according to claim 1 comprising administering a therapeutically effective amount of 4-{2-[5-methyl-1-(naphthalen-2-yl)-1H-pyrazol-3-yloxy] ethyl}morpholine hydrochloride and an opioid or opiate selected from the group consisting of morphine, tramadol, sufentanil, remifentanil, fentanyl, tapentadol, oxycodone, and buprenorphine.

4. A method for potentiating the analgesic effect of an opioid or opiate in a patient while also decreasing the dependency of the patient induced thereby when said opioid or opiate is administered in the prevention or treatment of pain that is a consequence of surgery, wherein said opioid or opiate is selected from the group consisting of morphine, tramadol, sufentanil, remifentanil, fentanyl, tapentadol, oxycodone, and buprenorphine, which comprises administering to the patient a therapeutically effective amount of 4-{2-[5-methyl-1-(naphthalen-2-yl)-1H-pyrazol-3-yloxy] ethyl}morpholine or a pharmaceutically acceptable salt, isomer or solvate thereof.

5. The method according to claim 4 comprising administering a therapeutically effective amount of 4-{2-[5-methyl-1-(naphthalen-2-yl)-1H-pyrazol-3-yloxy] ethyl}morpholine hydrochloride.

6. The method according to claim 1 comprising administering a therapeutically effective amount of 4-{2-[5-methyl-1-(naphthalen-2-yl)-1H-pyrazol-3-yloxy] ethyl}morpholine hydrochloride and morphine.

7. The method according to claim 1 comprising administering a therapeutically effective amount of 4-{2-[5-methyl-1-(naphthalen-2-yl)-1H-pyrazol-3-yloxy]ethyl}morpholine hydrochloride and tramadol.

8. The method according to claim 1 comprising administering a therapeutically effective amount of 4-{2-[5-methyl-1-(naphthalen-2-yl)-1H-pyrazol-3-yloxy]ethyl}morpholine hydrochloride and sufentanil.

9. The method according to claim 1 comprising administering a therapeutically effective amount of 4-{2-[5-methyl-1-(naphthalen-2-yl)-1H-pyrazol-3-yloxy]ethyl}morpholine hydrochloride and remifentanil.

10. The method according to claim 1 comprising administering a therapeutically effective amount of 4-{2-[5-methyl-1-(naphthalen-2-yl)-1H-pyrazol-3-yloxy]ethyl}morpholine hydrochloride and fentanyl.

11. The method according to claim 1 comprising administering a therapeutically effective amount of 4-{2-[5-methyl-1-(naphthalen-2-yl)-1H-pyrazol-3-yloxy]ethyl}morpholine hydrochloride and tapentadol.

12. The method according to claim 1 comprising administering a therapeutically effective amount of 4-{2-[5-methyl-1-(naphthalen-2-yl)-1H-pyrazol-3-yloxy]ethyl}morpholine hydrochloride and oxycodone.

13. The method according to claim 1 comprising administering a therapeutically effective amount of 4-{2-[5-methyl-1-(naphthalen-2-yl)-1H-pyrazol-3-yloxy]ethyl}morpholine hydrochloride and buprenorphine.

14. The method according to claim 1, wherein opiate or opioid and the 4-{2-[5-methyl-1-(naphthalen-2-yl)-1H-pyrazol-3-yloxy]ethyl}morpholine or a pharmaceutically acceptable salt, isomer or solvate thereof are administered simultaneously.

15. The method according to claim 1, wherein opiate or opioid and the 4-{2-[5-methyl-1-(naphthalen-2-yl)-1H-pyrazol-3-yloxy]ethyl}morpholine or a pharmaceutically acceptable salt, isomer or solvate thereof are administered sequentially.

16. The method according to claim 1, wherein opiate or opioid and the 4-{2-[5-methyl-1-(naphthalen-2-yl)-1H-pyrazol-3-yloxy]ethyl}morpholine or a pharmaceutically acceptable salt, isomer or solvate thereof are administered separately.

17. The method according to claim 1, wherein the 4-{2-[5-methyl-1-(naphthalen-2-yl)-1H-pyrazol-3-yloxy]ethyl}morpholine or a pharmaceutically acceptable salt, isomer or solvate thereof is administered at a dose of 2.5-80 mg/kg.

18. The method according to claim 1, wherein the 4-{2-[5-methyl-1-(naphthalen-2-yl)-1H-pyrazol-3-yloxy]ethyl}morpholine or a pharmaceutically acceptable salt, isomer or solvate thereof is administered at a dose of 2.5 mg/kg, 5 mg/kg, 10 mg/kg, 20 mg/kg, 40 mg/kg or 80 mg/kg.

* * * * *